(12) United States Patent
Gelfand et al.

(10) Patent No.: US 7,598,032 B2
(45) Date of Patent: Oct. 6, 2009

(54) THERMOSTABLE DNA POLYMERASES INCORPORATING NUCLEOSIDE TRIPHOSPHATES LABELED WITH FLUORESCENT DYES

(75) Inventors: David Harrow Gelfand, Oakland, CA (US); Lisa Vivian Kalman, San Francisco, CA (US); Fred Lawrence Reichert, Oakland, CA (US); Christopher Lim Sigua, Antioch, CA (US); Thomas W. Myers, Alameda, CA (US)

(73) Assignee: Roche Molecular Systems, Pleasanton, CA (US)

( * ) Notice: Subject to any disclaimer, the term of this patent is extended or adjusted under 35 U.S.C. 154(b) by 195 days.

(21) Appl. No.: 10/355,532

(22) Filed: Jan. 30, 2003

(65) Prior Publication Data

US 2003/0152988 A1   Aug. 14, 2003

Related U.S. Application Data

(63) Continuation of application No. 10/052,417, filed on Jan. 17, 2002, which is a continuation of application No. 09/146,631, filed on Sep. 3, 1998, now Pat. No. 6,346,379.

(60) Provisional application No. 60/058,525, filed on Sep. 11, 1997.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .......................... 435/6; 435/91.2
(58) Field of Classification Search ................. None
See application file for complete search history.

(56) References Cited

U.S. PATENT DOCUMENTS

| | | | |
|---|---|---|---|
| 4,889,818 A | 12/1989 | Gelfand et al. | |
| 5,338,678 A | 8/1994 | Senter et al. | |
| 5,418,155 A | 5/1995 | Cormier et al. | |
| 5,466,591 A | 11/1995 | Abramson et al. | |
| 5,545,548 A | 8/1996 | Senter et al. | |
| 5,571,706 A | 11/1996 | Baker et al. | |
| 5,614,365 A | 3/1997 | Tabor et al. | |
| 5,723,298 A * | 3/1998 | Oommen et al. | 435/6 |
| 5,852,191 A * | 12/1998 | Karandikar et al. | 546/13 |
| 5,939,292 A * | 8/1999 | Gelfand et al. | 435/91.2 |
| 6,083,686 A | 7/2000 | Sullivan | |
| 6,107,029 A * | 8/2000 | Giordano | 435/6 |
| 6,265,193 B1 * | 7/2001 | Brandis et al. | 435/194 |
| 2002/0164591 A1 * | 11/2002 | Brandis et al. | 435/6 |
| 2006/0088879 A1 * | 4/2006 | Brandis et al. | 435/6 |

FOREIGN PATENT DOCUMENTS

| | | |
|---|---|---|
| EP | 0 402 108 B1 | 12/1990 |
| EP | 0 482 714 B1 | 2/1992 |
| EP | 0 655 506 | 11/1994 |
| EP | 0727496 A2 | 8/1996 |
| EP | 0 823 479 | 7/1997 |
| EP | 0727496 A3 | 9/2000 |
| WO | WO 98/40496 | 3/1998 |

OTHER PUBLICATIONS

Kalman, L.V. Genome Sci. Technol. 1:42, 1995.*
Lomize (Lomize et al, Proteins: Structure, Function and Genetics, suppl. 3, pp. 199-203, 1999 : A Prediction of Protein Structure: The Problem of Fold Multiplicity).*
Beese et al., "Crystal structures of the Klenow Fragment of DNA polymerase I complexed with Deoxynucleoside Triphosphate and Pyrophosphate," *Biochemistry*, 1993, pp. 14095-14101, vol. 32.
Delarue et al., "An attempt to unify the structure of polymerases," *Protein Engineering*, 1990.
Donlin et al., "Mutants affecting nucleotide recognition by T7 DNA polymerase," *Biochemistry*, 1994, pp. 14908-14917, vol. 33.
Ito, et al., Compilation and alignment of DNA polymerase sequences, *Nucleic Acids Research*, 1991, pp. 4045-4057, vol. 19.
Lee, et al., "DNA sequencing with dye labeled terminators and t7 DNA polymerase: effect of dyes and dNTPs on incorporation of dye-terminators and probability analysis of termination fragments," *Nucleic Acids Research*, 1992, pp. 2471-2483, vol. 20.
Lomize, et al., "Prediction of protein structure: the problem of fold multiplicity," *Proteins: Structure, Function and Genetics*, 1999, pp. 199-203, Suppl. 3.
Polesky et al., "Side chains involved in catalysis of the polymerase reaction of DNA polymerase I from *Escherichia coli*," *The Journal of Biological Chemistry*, 1992, pp. 8417-8428, vol. 267.
Reeve, et al., "A Novel Thermostable Polymerase for DNA Sequencing," *Nature*, 1995, pp. 796-797, vol. 376.
Sanger, et al., "DNA Sequencing with chain-terminating inhibition," *PNAS*, 1977, pp. 5483-5467, vol. 74.
Voss, et al., "Automated Cycle Sequencing with Taquenase: Protocols for Internal Labeling, Dye Primer and "Doublex" Simultaneous Sequencing," *Biotechniques*, 1997, pp. 312-318, vol. 23.

* cited by examiner

*Primary Examiner*—Jehanne S Sitton
(74) *Attorney, Agent, or Firm*—Townsend and Townsend and Crew LLP

(57) ABSTRACT

Modified thermostable DNA polymerases having enhanced efficiency for incorporating unconventional nucleotides such as those labeled with fluorescein family dyes are advantageous in many in vitro DNA synthesis applications. Such enzymes are particularly useful for use in chain termination nucleic acid sequencing protocols, as are native forms of such enzymes. Genes encoding the modified enzymes and methods for their production and use offer cost and efficiency advantages for DNA sequencing.

10 Claims, 1 Drawing Sheet

SEQUENCE LISTING

<160> NUMBER OF SEQ ID NOS: 18

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Sequence
      Motif
<220> FEATURE:
<221> NAME/KEY: VARIANT
<222> LOCATION: (3)
<223> OTHER INFORMATION: Xaa at position 3 is any amino acid
<220> FEATURE:
<221> NAME/KEY: VARIANT
<222> LOCATION: (4)
<223> OTHER INFORMATION: Xaa at position 4 is any amino acid
<220> FEATURE:
<221> NAME/KEY: VARIANT
<222> LOCATION: (6)
<223> OTHER INFORMATION: Xaa at position 6 is any amino acid
<220> FEATURE:
<221> NAME/KEY: VARIANT
<222> LOCATION: (7)
<223> OTHER INFORMATION: Xaa at position 7 is Val or Ile
<220> FEATURE:
<221> NAME/KEY: VARIANT
<222> LOCATION: (9)
<223> OTHER INFORMATION: Xaa at position 9 is any amino acid
<220> FEATURE:
<221> NAME/KEY: VARIANT
<222> LOCATION: (10)
<223> OTHER INFORMATION: Xaa at position 10 is any amino acid

<400> SEQUENCE: 1

Leu Ser Xaa Xaa Leu Xaa Xaa Pro Xaa Xaa Glu
 1               5                  10

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Sequence
      Motif
<220> FEATURE:
<221> NAME/KEY: VARIANT
<222> LOCATION: (3)
<223> OTHER INFORMATION: Xaa at position 3 is Gln or Gly
<220> FEATURE:
<221> NAME/KEY: VARIANT
<222> LOCATION: (4)
<223> OTHER INFORMATION: Xaa at position 4 is any amino acid
<220> FEATURE:
<221> NAME/KEY: VARIANT
<222> LOCATION: (6)
<223> OTHER INFORMATION: Xaa at position 6 is Ser or Ala

<400> SEQUENCE: 2

Leu Ser Xaa Xaa Leu Xaa Ile Pro Tyr Glu Glu
 1               5                  10

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Sequence
      Motif
<220> FEATURE:
<221> NAME/KEY: VARIANT
<222> LOCATION: (4)

```
<223> OTHER INFORMATION: Xaa at position 4 is any amino acid

<400> SEQUENCE: 3

Leu Ser Gln Xaa Leu Ala Ile Pro Tyr Glu Glu
 1               5                  10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Sequence
      Motif
<220> FEATURE:
<221> NAME/KEY: VARIANT
<222> LOCATION: (4)
<223> OTHER INFORMATION: Xaa at position 4 is any amino acid
<220> FEATURE:
<221> NAME/KEY: VARIANT
<222> LOCATION: (7)
<223> OTHER INFORMATION: Xaa at position 7 is Val or Ile

<400> SEQUENCE: 4

Leu Ser Val Xaa Leu Gly Xaa Pro Val Lys Glu
 1               5                  10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Sequence
      Motif
<220> FEATURE:
<221> NAME/KEY: VARIANT
<222> LOCATION: (4)
<223> OTHER INFORMATION: Xaa at position 4 is any amino acid

<400> SEQUENCE: 5

Leu Ser Val Xaa Leu Gly Val Pro Val Lys Glu
 1               5                  10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Sequence
      Motif
<220> FEATURE:
<221> NAME/KEY: VARIANT
<222> LOCATION: (4)
<223> OTHER INFORMATION: Xaa at position 4 is any amino acid

<400> SEQUENCE: 6

Leu Ser Val Xaa Leu Gly Ile Pro Val Lys Glu
 1               5                  10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Sequence
      Motif
<220> FEATURE:
<221> NAME/KEY: VARIANT
<222> LOCATION: (3)
<223> OTHER INFORMATION: Xaa at position 3 is any amino acid
<220> FEATURE:
<221> NAME/KEY: VARIANT
```

```
<222> LOCATION: (4)
<223> OTHER INFORMATION: Xaa at position 4 is any amino acid but not a
      glutamic acid residue
<220> FEATURE:
<221> NAME/KEY: VARIANT
<222> LOCATION: (6)
<223> OTHER INFORMATION: Xaa at position 6 is any amino acid
<220> FEATURE:
<221> NAME/KEY: VARIANT
<222> LOCATION: (7)
<223> OTHER INFORMATION: Xaa at position 7 is Val or Ile
<220> FEATURE:
<221> NAME/KEY: VARIANT
<222> LOCATION: (9)
<223> OTHER INFORMATION: Xaa at position 9 is any amino acid
<220> FEATURE:
<221> NAME/KEY: VARIANT
<222> LOCATION: (10)
<223> OTHER INFORMATION: Xaa at position 10 is any amino acid

<400> SEQUENCE: 7

Leu Ser Xaa Xaa Leu Xaa Xaa Pro Xaa Xaa Glu
 1               5                  10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Sequence
      Motif
<220> FEATURE:
<221> NAME/KEY: VARIANT
<222> LOCATION: (2)
<223> OTHER INFORMATION: Xaa at position 2 is any amino acid
<220> FEATURE:
<221> NAME/KEY: VARIANT
<222> LOCATION: (3)
<223> OTHER INFORMATION: Xaa at position 3 is any amino acid
<220> FEATURE:
<221> NAME/KEY: VARIANT
<222> LOCATION: (4)
<223> OTHER INFORMATION: Xaa at position 4 is any amino acid except Glu
<220> FEATURE:
<221> NAME/KEY: VARIANT
<222> LOCATION: (5)
<223> OTHER INFORMATION: Xaa at position 5 is any amino acid
<220> FEATURE:
<221> NAME/KEY: VARIANT
<222> LOCATION: (6)
<223> OTHER INFORMATION: Xaa at position 6 is any amino acid
<220> FEATURE:
<221> NAME/KEY: VARIANT
<222> LOCATION: (7)
<223> OTHER INFORMATION: Xaa at position 7 is any amino acid
<220> FEATURE:
<221> NAME/KEY: VARIANT
<222> LOCATION: (8)
<223> OTHER INFORMATION: Xaa at position 8 is any amino acid
<220> FEATURE:
<221> NAME/KEY: VARIANT
<222> LOCATION: (9)
<223> OTHER INFORMATION: Xaa at position 9 is any amino acid
<220> FEATURE:
<221> NAME/KEY: VARIANT
<222> LOCATION: (10)
<223> OTHER INFORMATION: Xaa at position 10 is any amino acid

<400> SEQUENCE: 8

Leu Xaa Xaa Xaa Xaa Xaa Xaa Xaa Xaa Xaa Glu
 1               5                  10

<210> SEQ ID NO 9
<211> LENGTH: 11
<212> TYPE: PRT
```

<213> ORGANISM: Artificial Sequence
<220> FEATURE:
<223> OTHER INFORMATION: Description of Artificial Sequence: Sequence
      Motif
<220> FEATURE:
<221> NAME/KEY: VARIANT
<222> LOCATION: (2)
<223> OTHER INFORMATION: Xaa at position 2 is Ser or Ala
<220> FEATURE:
<221> NAME/KEY: VARIANT
<222> LOCATION: (3)
<223> OTHER INFORMATION: Xaa at position 3 is any amino acid
<220> FEATURE:
<221> NAME/KEY: VARIANT
<222> LOCATION: (4)
<223> OTHER INFORMATION: Xaa at position 4 is any amino acid except Glu
<220> FEATURE:
<221> NAME/KEY: VARIANT
<222> LOCATION: (5)
<223> OTHER INFORMATION: Xaa at position 5 is Leu or Ile
<220> FEATURE:
<221> NAME/KEY: VARIANT
<222> LOCATION: (6)
<223> OTHER INFORMATION: Xaa at position 6 is any amino acid
<220> FEATURE:
<221> NAME/KEY: VARIANT
<222> LOCATION: (7)
<223> OTHER INFORMATION: Xaa at position 7 is any amino acid
<220> FEATURE:
<221> NAME/KEY: VARIANT
<222> LOCATION: (8)
<223> OTHER INFORMATION: Xaa at position 8 is any amino acid
<220> FEATURE:
<221> NAME/KEY: VARIANT
<222> LOCATION: (9)
<223> OTHER INFORMATION: Xaa at position 9 is any amino acid
<220> FEATURE:
<221> NAME/KEY: VARIANT
<222> LOCATION: (10)
<223> OTHER INFORMATION: Xaa at position 10 is any amino acid

<400> SEQUENCE: 9

Leu Xaa Xaa Xaa Xaa Xaa Xaa Xaa Xaa Xaa Glu
 1               5                  10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Sequence
      Motif
<220> FEATURE:
<221> NAME/KEY: VARIANT
<222> LOCATION: (3)
<223> OTHER INFORMATION: Xaa at position 3 is any amino acid
<220> FEATURE:
<221> NAME/KEY: VARIANT
<222> LOCATION: (4)
<223> OTHER INFORMATION: Xaa at position 4 is any amino acid except Glu
<220> FEATURE:
<221> NAME/KEY: VARIANT
<222> LOCATION: (6)
<223> OTHER INFORMATION: Xaa at position 6 is any amino acid
<220> FEATURE:
<221> NAME/KEY: VARIANT
<222> LOCATION: (7)
<223> OTHER INFORMATION: Xaa at position 7 is any amino acid
<220> FEATURE:
<221> NAME/KEY: VARIANT
<222> LOCATION: (8)
<223> OTHER INFORMATION: Xaa at position 8 is any amino acid
<220> FEATURE:
<221> NAME/KEY: VARIANT
<222> LOCATION: (9)
<223> OTHER INFORMATION: Xaa at position 9 is any amino acid
<220> FEATURE:

```
<221> NAME/KEY: VARIANT
<222> LOCATION: (10)
<223> OTHER INFORMATION: Xaa at position 10 is any amino acid

<400> SEQUENCE: 10

Leu Ser Xaa Xaa Leu Xaa Xaa Xaa Xaa Xaa Glu
 1               5                  10

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: M13mp18
      template primer

<400> SEQUENCE: 11
gggaagggcg atcggtgcgg gcctcttcgc                                     30

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Sequence
      Motif
<220> FEATURE:
<221> NAME/KEY: VARIANT
<222> LOCATION: (4)
<223> OTHER INFORMATION: Xaa at position 4 is any amino acid
<220> FEATURE:
<221> NAME/KEY: VARIANT
<222> LOCATION: (5)
<223> OTHER INFORMATION: Xaa at position 5 is any amino acid
<220> FEATURE:
<221> NAME/KEY: VARIANT
<222> LOCATION: (7)
<223> OTHER INFORMATION: Xaa at position 7 is any amino acid
<220> FEATURE:
<221> NAME/KEY: VARIANT
<222> LOCATION: (8)
<223> OTHER INFORMATION: Xaa at position 8 is any amino acid
<220> FEATURE:
<221> NAME/KEY: VARIANT
<222> LOCATION: (11)
<223> OTHER INFORMATION: Xaa at position 11 is any amino acid
<220> FEATURE:
<221> NAME/KEY: VARIANT
<222> LOCATION: (12)
<223> OTHER INFORMATION: Xaa at position 12 is any amino acid
<220> FEATURE:
<221> NAME/KEY: VARIANT
<222> LOCATION: (13)
<223> OTHER INFORMATION: Xaa at position 13 is any amino acid

<400> SEQUENCE: 12

Met Arg Arg Xaa Xaa Lys Xaa Xaa Asn Tyr Xaa Xaa Xaa Tyr Gly
 1               5                  10                  15

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Sequence
      Motif
<220> FEATURE:
<221> NAME/KEY: VARIANT
<222> LOCATION: (3)
<223> OTHER INFORMATION: Xaa at position 3 is Gln or Gly
<220> FEATURE:
<221> NAME/KEY: VARIANT
<222> LOCATION: (4)
```

<223> OTHER INFORMATION: Xaa at position 4 is any amino acid except Glu
<220> FEATURE:
<221> NAME/KEY: VARIANT
<222> LOCATION: (6)
<223> OTHER INFORMATION: Xaa at position 6 is Ser or Ala

<400> SEQUENCE: 13

Leu Ser Xaa Xaa Leu Xaa Ile Pro Tyr Glu Glu
 1               5                  10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Sequence
      Motif
<220> FEATURE:
<221> NAME/KEY: VARIANT
<222> LOCATION: (4)
<223> OTHER INFORMATION: Xaa at position 4 is any amino acid except Glu

<400> SEQUENCE: 14

Leu Ser Gln Xaa Leu Ala Ile Pro Tyr Glu Glu
 1               5                  10

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Sequence
      Motif
<220> FEATURE:
<221> NAME/KEY: VARIANT
<222> LOCATION: (4)
<223> OTHER INFORMATION: Xaa at position 4 is any amino acid except Glu
<220> FEATURE:
<221> NAME/KEY: VARIANT
<222> LOCATION: (7)
<223> OTHER INFORMATION: Xaa at position 7 is Val or Ile

<400> SEQUENCE: 15

Leu Ser Val Xaa Leu Gly Xaa Pro Val Lys Glu
 1               5                  10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Sequence
      Motif
<220> FEATURE:
<221> NAME/KEY: VARIANT
<222> LOCATION: (4)
<223> OTHER INFORMATION: Xaa at position 4 is any amino acid except Glu

<400> SEQUENCE: 16

Leu Ser Val Xaa Leu Gly Val Pro Val Lys Glu
 1               5                  10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Sequence
      Motif
<220> FEATURE:
<221> NAME/KEY: VARIANT -continued

```
<222> LOCATION: (4)
<223> OTHER INFORMATION: Xaa at position 4 is any amino acid except Glu

<400> SEQUENCE: 17

Leu Ser Val Xaa Leu Gly Ile Pro Val Lys Glu
 1               5                   10

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Sequence
      Motif
<220> FEATURE:
<221> NAME/KEY: VARIANT
<222> LOCATION: (4)
<223> OTHER INFORMATION: Xaa at position 4 is any amino acid except Glu
<220> FEATURE:
<221> NAME/KEY: VARIANT
<222> LOCATION: (7)
<223> OTHER INFORMATION: Xaa at position 7 is Val or Ile

<400> SEQUENCE: 18

Ser Gln Ile Xaa Leu Arg Xaa
 1               5
```

THERMOSTABLE DNA POLYMERASES INCORPORATING NUCLEOSIDE TRIPHOSPHATES LABELED WITH FLUORESCENT DYES

This is a continuation of U.S. patent application Ser. No. 10/052,417, filed Jan. 17, 2002; which is a continuation of U.S. patent application Ser. No. 09/146,631, filed Sep. 3, 1998, and which issued as U.S. Pat. No. 6,346,379, which claims benefit of Provisional Application No. 60/058,525, filed Sep. 11, 1997, each of which is hereby incorporated by reference in its entirety.

FIELD OF THE INVENTION

The present invention relates to thermostable DNA polymerases which have enhanced efficiency for incorporating nucleoside triphosphates labeled with fluorescein family dyes. The present invention provides means for isolating and producing such altered polymerases. The enzymes of the invention are useful for many applications in molecular biology and are particularly advantageous for nucleic acid sequencing.

BACKGROUND OF THE INVENTION

Incorporation of nucleoside triphosphates (dNTPs) labeled with fluorescent dyes is important for many in vitro DNA synthesis applications. For example, dye-terminator DNA sequencing reactions require the incorporation of fluorescent dideoxynucleotide analogues for termination and labeling. In addition, in vitro synthesis of labeled products may involve incorporation of fluorescent nucleotides or nucleotide analogues. For example, fluorescently labeled DNA has been used in hybridization assays using microarrays of immobilized probes (Cronin et al., 1996, *Human Mutation* 7:244).

To assure fidelity of DNA replication, DNA polymerases have a very strong bias for incorporation of their normal substrates, referred to herein as conventional deoxynucleoside triphosphates (dNTPs), and against incorporation of unconventional dNTPs including dNTPs and dNTP analogues labeled with fluorescent dyes. In the cell, this property attenuates the incorporation of abnormal bases such as dUTP in a growing DNA strand. In vitro, this characteristic is particularly evident where both conventional and unconventional fluorescently-labeled nucleoside triphosphates are present, such as in DNA sequencing reactions using a version of the dideoxy chain termination method that utilizes dye-terminators (Lee et al., 1992, *Nuc. Acids. Res.* 20:2471 which is incorporated herein by reference).

Commercially available DNA cycle sequencing kits for dye-terminator methods use chain terminator ddNTPs labeled with fluorescent dyes of the rhodamine family.

However, rhodamine dyes are zwitterionic in charge and nucleoside triphosphates labeled with these dyes migrate anomalously in the electrophoretic gels used to separate the sequencing products for detection. This property of rhodamine family dyes necessitates making modifications in the standard sequencing protocol which include the use of dITP and an additional processing step before electrophoresis.

In contrast, negatively charged fluorescent dyes such as fluorescein family dyes allow 1) better separation between the labeled nucleoside triphosphates and labeled primer extension products, and 2) better electrophoretic migration of the labeled sequencing products than neutral or positively charged fluorescent dyes. Thus, the use of fluorescein family dyes avoids the need for additional processing steps required with the use of rhodamine family dyes. However, available dyes of the fluorescein family are not ideal for use in current commercially available DNA cycle sequencing formats because ddNTPs labeled with these dyes are not efficiently incorporated into sequencing products using these formats. Consequently, there is a need for commercially available thermostable DNA polymerases that can efficiently incorporate both conventional and fluorescein-labeled nucleotides. The present invention serves to meet that need. Further, an unexpected property of the mutant enzymes of this invention is the increased rate of primer extension relative to the corresponding wild-type enzyme. Another unexpected property is the increased uniformity of incorporation of the various terminator nucleotides in automated DNA sequence analysis.

SUMMARY OF THE INVENTION

The present invention provides template-dependent thermostable DNA polymerase enzymes having reduced discrimination against incorporation of nucleotides labeled with fluorescein family dyes compared to previously characterized enzymes. These enzymes incorporate nucleotides, including deoxynucleotides (dNTPs) and base analogues such as dideoxynucleotides (ddNTPs), that are labeled with fluorescein family dyes more efficiently than conventional thermostable enzymes. Genes encoding these enzymes are also provided by the present invention, as are recombinant expression vectors for providing large amounts of purified enzymes.

By the present invention, a region of criticality within thermostable DNA polymerases is identified which affects the polymerase's ability to incorporate nucleotides labeled with fluorescein family dyes, while retaining the ability to incorporate faithfully natural nucleotides. This region of criticality, or Critical Motif, can be introduced into genes for thermostable DNA polymerases by recombinant DNA methods such as site-specific mutagenesis to provide the advantages of the invention.

Thus, in one aspect, the invention provides recombinant thermostable DNA polymerase enzymes which are characterized in that the enzymes have been mutated to produce the Critical Motif and have reduced discrimination against incorporation of nucleotides labeled with fluorescein family dyes, in comparison to the corresponding wild-type enzyme.

In this aspect, the invention provides recombinant thermostable DNA polymerase enzymes which are characterized in that a) in its native form said polymerase comprises the amino acid sequence (given in one-letter code) LSXXLX(V/I) PXXE (SEQ ID NO: 1), where X is any amino acid; b) the X at position 4 in said sequence is mutated in comparison to said native sequence, except that X is not mutated to E; and c) said thermostable DNA polymerase has reduced discrimination against incorporation of nucleotides labeled with fluorescein family dyes in comparison to the native form of said enzyme. In the three-letter code, this amino acid sequence is represented as LeuSerXaaXaaLeuXaaXaaProXaaXaaGlu (SEQ ID NO: 1), whereby "Xaa" at positions 3, 4, 6, 9, and 10 of this sequence are any amino acid residue, and "Xaa" at position 7 of this sequence is Val or Ile.

In another embodiment, the recombinant thermostable DNA polymerases are characterized in that a) the native form of the polymerase comprises the amino acid sequence LS(Q/G)XL(S/A)IPYEE (SEQ ID NO: 2), where X is any amino acid; b) the X at position 4 in said sequence is mutated in comparison to said native sequence, except that X is not mutated to E; and c) said thermostable DNA polymerase has reduced discrimination against incorporation of nucleotides labeled with fluorescein family dyes in comparison to the native form of said enzyme. In the three-letter code, this amino acid sequence is represented as LeuSerXaaXaaLeuXaaIleProTyrGluGlu (SEQ ID NO: 2), whereby "Xaa" at position 3 is Gln or Gly, "Xaa" at position 4 is any amino acid, and "Xaa" at position 6 is Ser or Ala. In a preferred embodiment, the amino acid sequence is LSQXLAIPYEE (SEQ ID NO:3), where X is any amino acid. In the three-letter code, this amino acid sequence is represented as LeuSerGlnXaaLeuAlaIleProTyrGluGlu (SEQ ID NO:3), whereby "Xaa" at position 4 is any amino acid. In a more preferred embodiment, the "Xaa" at position 4 is Lys.

In yet another embodiment, the recombinant thermostable DNA polymerases are characterized in that a) the native form of the polymerase comprises the amino acid sequence LSVXLG(V/I)PVKE (SEQ ID NO: 4); b) the X at position 4 in said sequence is mutated in comparison to said native sequence, except that X is not mutated to E; and c) said thermostable DNA polymerase has reduced discrimination against incorporation of nucleotides labeled with fluorescein family dyes in comparison to the native form of said enzyme. In the three-letter code, this amino acid sequence is represented as LeuSerValXaaLeuGlyXaaProValLysGlu (SEQ ID NO: 4), whereby "Xaa" at position 4 is any amino acid and "Xaa" at position 7 is Val or Ile. In a preferred embodiment, the amino acid sequence is LSVXLGVPVKE (SEQ ID NO: 5) where X at position 4 is any amino acid. In the three-letter code, this amino acid sequence is represented as LeuSerValXaaLeuGlyValProValLysGlu (SEQ ID NO: 5), whereby "Xaa" at position 4 is any amino acid. In a more preferred embodiment, the "Xaa" at position 4 is Arg. In another preferred embodiment, the amino acid sequence is LSVXLGIPVKE (SEQ ID NO: 6) where X at position 4 is any amino acid. In the three-letter code, this amino acid sequence is represented as LeuSerValXaaLeuGlyIleProValLysGlu (SEQ ID NO: 6), whereby "Xaa" at position 4 is any amino acid. In a more preferred embodiment, the "Xaa" at position 4 is Arg.

In another aspect of this invention, the particular region of criticality of this invention can be combined with motifs in other regions of the polymerase gene that are known to provide thermostable DNA polymerases with reduced discrimination against incorporation of unconventional nucleotides such as rNTPs and ddNTPs. As exemplified herein, a recombinant *Thermus aquaticus* (Taq) DNA polymerase enzyme containing two mutations was constructed. The first mutation was an E to K mutation in the X residue at position 4 of the critical motif of this invention. The second mutation was a mutation allowing more efficient incorporation of ddNTPs known as the F667Y mutation. This mutation is a phenylalanine to tyrosine mutation at position 667 of Taq DNA polymerase (described in U.S. Pat. No. 5,614,365 and U.S. Ser. No. 8/448,223 and herein incorporated by reference). When used in a sequencing reation with fluorescein dye family-labeled ddNTPs, the E681K F667Y double mutant enzyme was found to produce a readable sequencing ladder. Thus, in one embodiment, a motif conferring reduced discrimination toward dideoxynucleotides is combined with the critical motif of this invention to provide an enzyme having an increased efficiency of incorporation of both labeled and unlabeled ddNTPs.

In addition, the E681K F667Y mutant enzyme was unexpectedly found to exhibit a significantly increased extension rate relative to an enzyme with the F667Y mutation alone. Thus, in another embodiment of the invention, introduction of the critical motif into a thermostable DNA polymerase enzyme, alone or in combination with other motifs, produces enzymes having an increased extension rate. The double mutant enzyme was also unexpectedly found to produce more uniform peak heights in dye-terminator dideoxy-sequencing using rhodamine-labeled terminators. Thus, in yet another embodiment, introduction of the critical motif into a thermostable DNA polymerase enzyme produces enzymes displaying more uniform peak heights in DNA sequencing methods using rhodamine dye family labeled terminators.

In another embodiment, a mutation allowing more efficient incorporation of rNTPs, such as the glutamic acid to glycine mutation at position 615 of Taq DNA polymerase, or E615G mutation (described in U.S. Ser. No. 60/023,376, filed Sep. 6, 1996, and herein incorporated by reference), is combined with the critical motif of this invention to provide an enzyme having an increased efficiency of incorporation of ribonucleotides labeled with fluorescein family dyes.

In another aspect of this invention, genes encoding the polymerases of this invention are also provided. Specifically, genes encoding recombinant thermostable polymerases comprising the critical motif of this invention are provided. Also included in this aspect are genes encoding combinations of two or more mutations that include mutations producing the critical motif of this invention.

In yet another aspect, the invention also provides improved methods of DNA sequencing that allow the use of lower concentrations of fluorescein dye family-labeled ddNTPs, thereby reducing the cost of performing the reactions. The improved methods of the invention also allow the use of lower ratios of fluorescein dye family-labeled ddNTPs to dNTPs. Use of these methods results in numerous advantages, including more efficient polymerization, lower concentrations of template nucleic acid being required, and a decreased likelihood of introducing inhibitors into the reaction mix. These advantages also facilitate the sequencing of long templates. The invention also provides improved methods of sequencing wherein sequencing reactions can be loaded directly onto sequencing gels for subsequent electrophoresis without intermediate purification.

Thus, in one embodiment of the invention, the invention provides improved methods for determining the sequence of a target nucleic acid using a recombinant enzyme which has a) a mutation at position 4 which produces the critical motif of this invention and b) has reduced discrimination against incorporation of nucleotides labeled with fluorescein family dyes in comparison with the corresponding wild-type enzyme. Also within the scope of this invention are improved sequencing methods using thermostable DNA polymerase enzymes derived from thermophilic species, where the enzymes contain naturally occurring sequence variations that produce the critical motif of this invention. These native enzymes can also provide reduced discrimination against incorporation of unconventional nucleotides. In this embodiment, the invention provides improved methods of sequencing using a native thermostable DNA polymerase a) having the critical motif of this invention wherein the amino acid in position 4 is not Glu and b) having reduced discrimination against incorporation of nucleotides labeled with fluorescein family dyes.

Also within the scope of this invention are improved methods of producing DNA labeled with fluorescein family dyes. The enzymes of the invention efficiently incorporate fluorescein-labeled dNTPs in a polymerase chain reaction method, producing amplified products that are labeled at various sites with fluorescein family dyes. Thus, in one embodiment, an improved method of labeling DNA comprises a) providing a reaction mixture comprising dNTPs labeled with fluorescein family dyes and an enzyme of the invention and b) performing a nucleic acid amplification reaction.

The enzymes of the invention, and genes encoding these enzymes, provide additional aspects of the invention which are kits for DNA sequencing that comprise a recombinant enzyme of the invention and may additionally include a negatively charged fluorescent terminator compound. Other kits for DNA sequencing comprise a) a negatively charged fluorescent terminator compound and b) a native enzyme of the invention.

The invention also provides kits for producing labeled DNA which comprise a recombinant enzyme of the invention. Other kits for producing labeled DNA comprise a) a negatively charged fluorescent nucleoside triphosphate compound and b) a native enzyme of the invention.

DETAILED DESCRIPTION OF THE INVENTION

Figure 1:
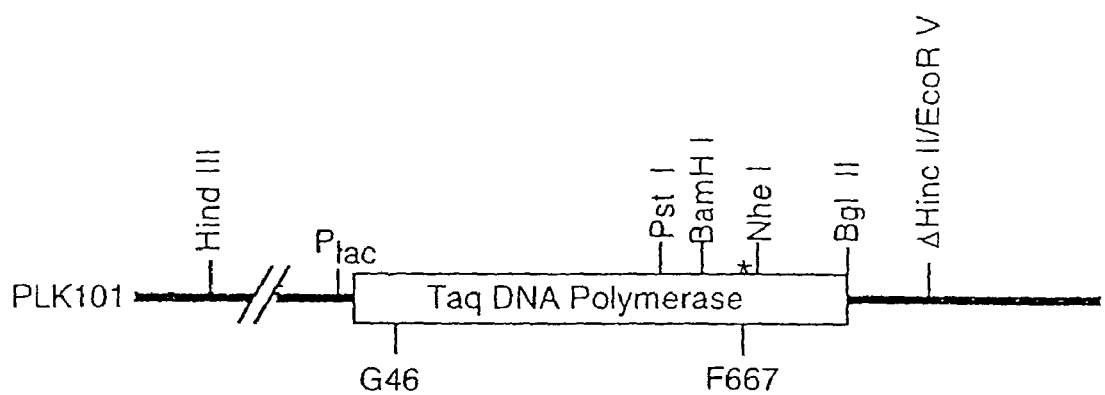
FIG. 1 is a schematic representation of the Taq DNA polymerase gene. Restriction sites are indicated that relate to Example I and the description of methods for preparing additional mutants and expression vectors provided herein.

To facilitate understanding of the invention, a number of terms are defined below.

The term "gene" refers to a DNA sequence that comprises control and coding sequences necessary for the production of a recoverable bioactive polypeptide or precursor. The polypeptide can be encoded by a full-length gene sequence or by any portion of the coding sequence so long as the enzymatic activity is retained.

The term "native" refers to a gene or gene product which is isolated from a naturally occurring source. This term also refers to a recombinant form of the native protein produced by molecular biological techniques which has an amino acid sequence identical to that of the native form.

The term "mutant" refers to a gene that has been altered in its nucleic acid sequence or a gene product which has been altered in its amino acid sequence, resulting in a gene product which may have altered functional properties when compared to the native or wild-type gene or gene product. Such alterations include point mutations, deletions and insertions.

The term "host cell(s)" refers to both single-cellular prokaryote and eukaryote organisms such as bacteria, yeast, and actinomycetes and single cells from higher order plants or animals when being grown in cell culture.

The term "expression system" refers to DNA sequences containing a desired coding sequence and control sequences in operable linkage, so that host cells transformed with these sequences are capable of producing the encoded proteins. To effect transformation, the expression system may be included on a vector; however, the relevant DNA may also be integrated into the host chromosome.

The term "oligonucleotide" as used herein is defined as a molecule comprised of two or more deoxyribonucleotides or ribonucleotides, preferably more than three, and usually more than ten. The exact size of an oligonucleotide will depend on many factors, including the ultimate function or use of the oligonucleotide.

Oligonucleotides can be prepared by any suitable method, including, for example, cloning and restriction of appropriate sequences and direct chemical synthesis by a method such as the phosphotriester method of Narang et al., 1979, *Meth. Enzymol.* 68:90-99; the phosphodiester method of Brown et al., 1979, *Meth. Enzymol.* 68:109-151; the diethylphosphoramidite method of Beaucage et al., 1981, *Tetrahedron Lett.* 22:1859-1862; the triester method of Matteucci et al., 1981, *J. Am. Chem. Soc.* 103:3185-3191 or automated synthesis methods; and the solid support method of U.S. Pat. No. 4,458,066, which publications are each incorporated herein by reference.

The term "primer" as used herein refers to an oligonucleotide, whether natural or synthetic, which is capable of acting as a point of initiation of synthesis when placed under conditions in which primer extension is initiated. A primer is preferably a single-stranded oligodeoxyribonucleotide. The appropriate length of a primer depends on the intended use of the primer but typically ranges from 15 to 35 nucleotides. Short primer molecules generally require cooler temperatures to form sufficiently stable hybrid complexes with the template. A primer need not reflect the exact sequence of the template but must be sufficiently complementary to hybridize with a template for primer elongation to occur.

A primer can be labeled, if desired, by incorporating a label detectable by spectroscopic, photochemical, biochemical, immunochemical, or chemical means. For example, useful labels include $^{32}$P, fluorescent dyes, electron-dense reagents, enzymes (as commonly used in ELISA assays), biotin, or haptens and proteins for which antisera or monoclonal antibodies are available.

The term "thermostable polymerase," refers to an enzyme which is stable to heat, is heat resistant and retains sufficient activity to effect subsequent primer extension reactions and does not become irreversibly denatured (inactivated) when subjected to the elevated temperatures for the time necessary to effect denaturation of double-stranded nucleic acids. The heating conditions necessary for nucleic acid denaturation are well known in the art and are exemplified in U.S. Pat. Nos. 4,683,202 and 4,683,195, which are incorporated herein by reference. As used herein, a thermostable polymerase is suitable for use in a temperature cycling reaction such as the polymerase chain reaction ("PCR"). Irreversible denaturation for purposes herein refers to permanent and complete loss of enzymatic activity. For a thermostable polymerase, enzymatic activity refers to the catalysis of the combination of the nucleotides in the proper manner to form primer extension products that are complementary to a template nucleic acid strand.

The term "conventional" or "natural" when referring to nucleic acid bases, nucleoside triphosphates, or nucleotides refers to those which occur naturally in the polynucleotide being described (i.e., for DNA these are dATP, dGTP, dCTP and dTTP). Additionally, dITP, and 7-deaza-dGTP are frequently utilized in place of dGTP and 7-deaza-dATP can be utilized in place of dATP in in vitro DNA synthesis reactions, such as sequencing. Collectively these may be referred to as dNTPs.

The term "unconventional" or "modified" when referring to a nucleic acid base, nucleoside, or nucleotide includes modification, derivations, or analogues of conventional bases, nucleosides, or nucleotides that naturally occur in a particular polynucleotide. The deoxyribonucleotide form of uracil is an unconventional or modified base in DNA (dUMP), whereas, the ribonucleotide form of uracil is a conventional base in RNA (UMP). As used herein, unconventional nucleotides include but are not limited to compounds used as terminators for nucleic acid sequencing. Terminator compounds include but are not limited to those compounds which have a 2',3' dideoxy structure and are referred to as dideoxynucleoside triphosphates. The dideoxynucleoside triphosphates ddATP, ddTTP, ddCTP and ddGTP are referred to collectively as ddNTPs. Other unconventional nucleotides include phosphorothioate dNTPs ([α-S]dNTPs), 5'-α-borano-dNTPs, α-methyl-phosphonate dNTPs, and ribonucleoside triphosphates (rNTPs). Unconventional bases may be labeled with radioactive isotopes such as $^{32}$P, $^{33}$P, or $^{35}$S; fluorescent labels; chemiluminescent labels; bioluminescent labels; hapten labels such as biotin; or enzyme labels such as streptavidin or avidin. Fluorescent labels may include dyes that are negatively charged, such as dyes of the fluorescein family, or dyes that are neutral in charge, such as dyes of the rhodamine family, or dyes that are positively charged, such as dyes of the cyanine family. Dyes of the fluorescein family include e.g., FAM, HEX, TET, JOE, NAN and ZOE. Dyes of the rhodamine family include Texas Red, ROX, R110, R6G, and TAMRA. FAM, HEX, TET, JOE, NAN, ZOE, ROX, R110, R6G, and TAMRA are marketed by Perkin-Elmer (Foster City, Calif.), and Texas Red is marketed by Molecular Probes. Dyes of the cyanine family include Cy2, Cy3, Cy5, and Cy7 and are marketed by Amersham (Amersham Place, Little Chalfont, Buckinghamshire, England).

The term "DNA synthesis reaction" refers to methods of producing copies of DNA including but not limited to PCR, strand displacement amplification, transcription mediated amplification, primer extension and reverse transcription.

In order to further facilitate understanding of the invention, specific thermostable DNA polymerase enzymes and fluorescent dyes are referred to throughout the specification to exemplify the invention, and these references are not intended to limit the scope of the invention.

The present invention provides novel and improved compositions which are thermostable DNA polymerases. The enzymes of the invention include recombinant polymerases which more efficiently incorporate nucleoside triphosphates labeled with fluorescein family dyes in comparison to the corresponding wild-type enzymes. The thermostable DNA polymerases of the invention are more suitable and desirable for use in processes such as DNA sequencing and in vitro synthesis of labeled products than prior art polymerases. Improved DNA sequencing methods of the invention include the use of these recombinant polymerases as well as the use of native enzymes which more efficiently incorporate nucleoside triphosphates labeled with fluorescein family dyes than previously characterized enzymes. DNA sequences encoding these enzymes, and vectors for expressing the proteins are also provided.

The thermostable DNA polymerases of the invention possess a region of criticality within the amino acid sequence of the polymerase activity domain of the enzyme. The critical region within the amino acid sequence of a thermostable DNA polymerase provided by the present invention is shown below using the conventional single-letter amino acid code (Lehninger, *Biochemistry*, New York, N.Y., Worth Publishers Inc., 1970, page 67, which is incorporated herein by reference).

SEQ ID NO: 7 LSXXLX(V/I)PXXE where the "X" at position 4 indicates any amino acid except E. In the three-letter code for amino acids, this sequence is represented as LeuSerXaaXaaLeuXaaXaaproXaaXaaGlu (SEQ ID NO: 7) whereby "Xaa" at positions 3, 6, 9, and 10 is any amino acid, "Xaa" at position 4 of this sequence is any amino acid but not a glutamic acid residue (Glu) and "Xaa" at position 7 is Val or Ile. This region of criticality provides thermostable DNA polymerase enzymes characterized by the ability to efficiently incorporate nucleotides labeled with fluorescein family dyes.

For example, in a derivative of the *Thermus aquaticus* (Taq) DNA polymerase gene which already contains a gly-cine to aspartic acid mutation at position 46 (G46D) and an F667Y mutation, a mutation of G to A in the first position of the codon for glutamic acid at residue 681 sequence of the full length Taq DNA polymerase sequence (corresponding to position 4 of the critical motif) results in an enzyme having the critical motif. This enzyme displays 1) an approximately a 2- to 10-fold increase in the efficiency of incorporation of nucleotides labeled with fluorescein family dyes with no impairment of the enzyme's ability to mediate PCR in the presence of conventional nucleotides and 2) a 3 to 4.3-fold increase in the extension rate. In Taq DNA polymerase this particular mutation results in an amino acid change of E (glutamic acid) to K (lysine).

Although this particular amino acid change produced the critical motif and significantly alters the ability of the enzyme to incorporate unconventional nucleotides, it is expected that the specific change of E to K is not as critical to the invention as is the now identified position within the region of criticality. Thus, in a preferred embodiment, the invention provides recombinant thermostable DNA polymerase enzymes which are characterized in that a) in its native form said polymerase comprises the amino acid sequence LSXXLX(V/I)PXXE (SEQ ID NO: 1), where X is any amino acid; b) the X at position 4 in said sequence is mutated in comparison to said native sequence, except that the X at position 4 is not mutated to E; and c) said thermostable DNA polymerase has reduced discrimination against incorporation of nucleotides labeled with fluorescein family dyes in comparison to the native form of said enzyme. In a more preferred embodiment, the X at position 4 is replaced by an amino acid having a positive charge, such as K, R or H, or by a polar amino acid such as Q or N. In a most preferred embodiment, the X at position 4 is replaced by K.

In another preferred embodiment of the invention, the of the invention is characterized in that the enzyme (a) has reduced discrimination against fluorescein dye family labeled nucleotides and (b) comprises the amino acid sequence LS(Q/G)XL(S/A)IPYEE where X is any amino acid (SEQ ID NO: 2). In three-letter code, this amino acid sequence is represented as LeuSerXaaXaaLeuXaaIleProTyrGluGlu, whereby "Xaa" at position 3 is Gln or Gly, "Xaa" at position 4 is any amino acid, and "Xaa" at position 6 is Ser or Ala.

In a more preferred embodiment of the invention, the enzyme having reduced discrimination against fluorescein dye family labeled nucleotides comprises the amino acid sequence LSQXLAIPYEE where X is any amino acid (SEQ ID NO: 3). In the three-letter code, this amino acid sequence is represented as LeuSerGlnXaaLeuAlaIleProTyrGluGlu, whereby "Xaa" at position 4 is any amino acid. In a most preferred embodiment of the invention, the X is a K residue.

In another preferred embodiment of the invention, the the enzyme having reduced discrimination against fluorescein dye family labeled nucleotides comprises the amino acid sequence LSVXLG(V/I)PVKE where X is any amino acid (SEQ ID NO: 4). In the three-letter code, this amino acid sequence is represented as LeuSerValXaaLeuGlyXaaProValLysGlu, whereby "Xaa" at position 4 is any amino acid and "Xaa" at position 7 is Val or Ile.

In a more preferred embodiment of the invention, the enzyme having reduced discrimination against fluorescein dye family labeled nucleotides comprises the amino acid sequence LSVXLGVPVKE where X is any amino acid (SEQ ID NO: 5). In the three-letter code, this amino acid sequence is represented as LeuSerValXaaLeuGlyValProValLysGlu, whereby "Xaa" at position 4 is any amino acid. In a most preferred embodiment, the X is an R residue.

In another more preferred embodiment, the enzyme having reduced discrimination against fluorescein dye family labeled nucleotides comprises the amino acid sequence LSVXL-GIPVKE where X is any amino acid (SEQ ID NO: 6). In the three-letter code, this amino acid sequence is represented as LeuSerValXaaLeuGlyIleProValLysGlu, whereby "Xaa" at position 4 is any amino acid. In a most preferred embodiment, the X is an R residue.

The characterization of the E681K mutation described herein identified a region in the DNA polymerase gene that affects the ability of the polymerase to interact with negatively charged fluorescent nucleotides. This site, distal to helix O, is at the end of the $O_a$ helix and the beginning of the $O_b$ helix of the polymerase (Kim, et al., 1995, *Nature*, 376: 612). Based on molecular modeling principles well-known in the art, changes in the structure of the $O_a$–$O_b$ helix other than E to K at position 681 are also expected to produce changes in the ability of the polymerase to discriminate against nucleotides labeled with fluorescein family dyes. Thus, mutations at positions in the critical motif other than those in the X residue at position 4 are also within the scope of this invention. In this embodiment, the invention provides a recombinant thermostable DNA polymerase enzyme which is characterized in that (a) in its native form, the polymerase comprises the amino acid sequence LSXXLX(V/I)PXXE (SEQ ID NO: 1) where X is any amino acid, (b) the recombinant polymerase comprises at least one mutation within the amino acid sequence, except that X at position 4 is not mutated to E, and c) the enzyme has reduced discrimination against incorporation of nucleotides labeled with fluorescein family dyes, in comparison to the corresponding native enzyme.

Similarly, thermostable DNA polymerases that comprise critical motifs that are similar, but not identical to the critical motif that is amino acid sequence LSXXLX(V/I)PXXE (SEQ ID NO: 7) where X at position 4 is any amino acid except E, are within the scope of this invention. Specifically, in one embodiment, the critical motif is the amino acid sequence LXXXXXXXXXE (SEQ ID NO: 8) where X at position 4 is any amino acid except E. In the three letter code, this amino acid sequence is represented as LeuXaaXaaXaaXaaXaaXaaXaaXaaXaaGlu (SEQ ID NO: 8), whereby "Xaa" at positions 2, 3, 5, 6, 7, 8, 9 and 10 are any amino acid and "Xaa" at position 4 is any amino acid except Glu.

In another embodiment, the critical motif is amino acid sequence L(S/A)XX(L/I)XXXXXE (SEQ ID NO: 9) where X at position 4 is any amino acid except E. In the three-letter code, this amino acid sequence is represented as LeuXaaXaaXaaXaaXaaXaaXaaXaaGlu (SEQ ID NO: 9), whereby "Xaa" at positions 3, 6, 7, 8, 9, and 10 are any amino acid, "Xaa" at position 2 is Ser or Ala, "Xaa" at position 4 is any amino acid except Glu, and "Xaa" at position 5 is Leu or Ile.

In yet another embodiment, the critical motif is amino acid sequence LSXXLXXXXXE (SEQ ID NO: 10) where X at position 4 is any amino acid except E. In the three-letter code, this amino acid sequence is represented as LeuSerXaaXaaLeuXaaXaaXaaXaaXaaGlu (SEQ ID NO: 10), whereby "Xaa" at positions 3, 6, 7, 8, 9, and 10 are any amino acid and "Xaa" at position 4 is any amino acid except Glu.

The ability of the enzymes of this invention to efficiently incorporate nucleotides labeled with fluorescein family dyes is measured by ddNTP incorporation assays. One such assay is a primer extension competition assay conducted under conditions of limiting template. In this assay, a primer DG48 (5'-GGGAAGGGCGATCGGTGCGGGCCTCTTCGC), (SEQ ID NO: 11), bound to M13 mp18 template (Innis et al., 1988, *Proc. Natl. Acad. Sci. USA* 85:9436) is extended in the presence of [α-$^{33}$P]dCTP and excess enzyme with various levels of a fluorescently labeled ddNTP, Zowie-ddCTP. Because the incorporation of a ddCTP residue terminates the extension reaction, the more readily a DNA polymerase incorporates a ddCTP into an extended primer, the less [α-$^{33}$P]dCTP can be incorporated. Thus, as the efficiency of fluorescently labeled ddCTP incorporation increases, the extent of inhibition of DNA synthesis is increased. The reactions were also performed with various levels of an unlabeled ddCTP. The concentrations of ddCTP and Zowie-ddCTP needed for 50% inhibition were calculated and compared to give a relative measure of the ability of the enzyme to incorporate the fluorescently-labeled nucleotide. The details of the ddNTP incorporation assay are provided in Example II.

Thus, in one embodiment of the invention, the characteristic of reduced discrimination against incorporation of nucleotides labeled with fluorescein family dyes is measured by the fluorescent ddNTP incorporation assay described in Example II. In a preferred embodiment, the concentration of a ddNTP labeled with a fluorescein dye, Zowie-ddCTP, required for 50% inhibition of DNA synthesis is reduced at least 3-fold for a mutant enzyme of the invention, relative to the wild-type enzyme. In a more preferred embodiment, the concentration is reduced at least 5-fold. In a most preferred embodiment, the concentration is reduced at least 10-fold. In another embodiment, the characteristic of reduced discrimination is assayed by measuring fluorescent dNTP incorporation.

In another aspect of the invention, the thermostable DNA polymerase gene sequence and enzyme are derived from various thermophilic species. In one embodiment, the polymerase gene sequence and enzyme are from a species of the genus *Thermus*. In other embodiments of the invention, the gene sequence and enzyme are from thermophilic species other than *Thermus*. The full nucleic acid and amino acid sequence for numerous thermostable DNA polymerases are available. The sequences each of Taq, *Thermus thermopilus* (Tth), *Thermus* species Z05, *Thermus* species sps17, *Thermotoga maritima* (Tma), and *Thermosipho africanus* (Taf) polymerase have been published in PCT International Patent Application No. PCT/U.S.91/07035 which published as PCT Patent Publication No. WO 92/06200 on Apr. 16, 1992, and is incorporated herein by reference. The sequences for the DNA polymerase from *Thermus flavus*, *Bacillus caldotenax*, and *Bacillus stearothermophilus* have been published in Akhmetzjanov and Vakhitov, 1992, *Nucleic Acids Research* 20 (21):5839, Uemori et al., 1993, *J. Biochem.* 113:401-410, and as accession number BSU23149.ng from the NG:New GenBank database, respectively, which are each incorporated herein by reference. The sequence of the thermostable DNA polymerase from *Thermus caldophilus* is found in EMBL/GenBank Accession No. U62584. The sequence of the thermostable DNA polymerase from *Thermus filiformis* can be recovered from ATCC Deposit No. 42380 using the methods provided in U.S. Pat. No. 4,889,818, as well as the sequence information provided in Table 1. The sequence of the *Thermotoga neapolitana* DNA polymerase is from GeneSeq Patent Data Base Accession No. R98144 and PCT WO 97/09451

TABLE I

| Organism | | | | Critical Motif ⇓ | | | | | | | | Critical Amino Acid Position |
|---|---|---|---|---|---|---|---|---|---|---|---|---|
| Consensus | L | S/a | - | - | L/i | - | - | - | - | - | E | |
| *Thermus aquaticus* | L | S | Q | E | L | A | I | P | Y | E | E | 681 |
| *Thermus flavus* | L | S | G | E | L | S | I | P | Y | E | E | 679 |
| *Thermus thermophilus* | L | S | Q | E | L | A | I | P | Y | E | E | 683 |
| *Thermus specie Z05* | L | S | Q | E | L | A | I | P | Y | E | E | 683 |
| *Thermus specie sps17* | L | S | Q | E | L | S | I | P | Y | E | E | 679 |
| *Thermus caldophilus* | L | S | Q | E | L | A | I | P | Y | E | E | 683 |
| *Thermus filiformis* | L | S | Q | E | L | S | I | P | Y | E | E | 679 |
| *Thermotoga maritima* | L | S | V | R | L | G | V | P | V | K | E | 744 |
| *Thermotoga neapolitana* | L | S | V | R | L | G | I | P | V | K | E | 744 |
| *Thermosipho africanus* | L | S | K | R | I | G | L | S | V | S | E | 743 |
| *Bacillus caldoenax*[1] | L | A | Q | N | L | N | I | S | R | K | E | 725, 724 |
| *Bacillus stearothermophilus*[2] | L | A | Q | N | L | N | I | T | R | K | E | 724, 727, 802 |

1. Protein sequence from Accession No. D12982, Uemori T., Ishino Y., Fujita K., Asada K., Kato I. "Cloning of the DNA polymerase gene of *Bacillus caldotenax* and characterization of the gene product" *J. Biochem.* 113:401 (1993). The critical residue in that sequence is 725. An almost identical protein sequence is provided as a putative "*Bacillus stearothermophilus*" DNA Polymerase in Accession No. R45155 and WPI 93-408323/51. The critical residue in that sequence is 724.
2. There are several sequence submissions for *Bacillus stearothermophilus* DNA polymerase in the GeneBank, or SwissProt/PIR databases. Although these sequences are highly related, but somewhat different from one another, each contains the identical L(S/A)XX(L/I)XXXXXE (SEQ ID NO: 9) motif, where X is any amino acid except E. In the three-letter code, this amino acid sequence is represented as LeuXaaXaaXaaXaaXaaXaaXaaXaaGlu (SEQ ID NO: 9), whereby "Xaa" at positions 3, 6, 7, 8, 9, and 10 are any amino acid, "Xaa" at position 2 is Ser or Ala, "Xaa" at position 4 is any amino acid except Glu, and "Xaa" at position 5 is Leu or Ile. In the table above, protein sequences comprising the Critical Residue in the Critical Motif at position 724 are provided by Japanese patent publication J 05 304 964A, EP No. 699,760, and Accession No. U33536. Another highly related, but somewhat different, protein sequence was published in *Gene* 163:65-68 (1995), contains the Critical Residue in the Critical Motif at position 727. Another highly related, but somewhat different, protein sequence, Accession No. U23149, for Bst DNA polymerase contains the Critical Residue in the Critical Motif at position 802.

Because the DNA polymerases of each thermophilic species are unique, the amino acid position of the region of criticality is distinct for each enzyme. Amino acid and nucleic acid sequence alignment programs are readily available and, given the particular region identified herein, serve to assist in the identification of the exact sequence region of the invention. Such sequence alignment programs are available from the Genetics Computer Group, 575 Science Drive, Madison, Wis. Given the particular motif identified herein, these programs, including "GAP," "BESTFIT," and "PILEUP," serve to assist in the localization of the critical motif. The position of the regions of criticality are shown in Table I for thermostable DNA polymerases from exemplary thermophilic species.

Regardless of the exact position of the critical motif LSXXLX(V/I)PXXE (SEQ ID NO: 7), where X at position 4 is any amino acid except E, within the polymerase domain of a thermostable DNA polymerase, the presence of the motif serves to provide thermostable DNA polymerases having the ability to efficiently incorporate nucleotides labeled with fluorescein family dyes. Therefore, mutation of the conserved glutamic acid of the thermostable DNA polymerases of *Thermus flavus* (Glu 679), *Thermus thermophilus* (Glu 683), *Thermus* species Z05 (Glu 683), *Thermus* species sps17 (Glu 679) *Thermus caldophilus* (Glu 683), *Thermus filiformis* (Glu 679) to produce the critical motif will provide an enhancing effect on the ability of the polymerase to efficiently incorporate nucleotides labeled with fluorescein family dyes.

In addition, in view of the highly conserved nature of the now identified critical motif, novel thermostable DNA polymerases may be identified based upon their homology to, for example, Taq DNA polymerase or the sequences of other DNA polymerases in Table I (see for example U.S. Pat. Nos. 5,618,711 and 5,624,833 which are herein incorporated by reference). Such polymerases, so long as their peptide sequence is at least 45% and most preferably greater than 80% homologous to the Taq polymerase amino acid sequence, as determined by the methods described herein, are within the scope of the present invention. Consequently, the invention relates to a class of enzymes which also includes, for example, the thermostable DNA polymerase, and corresponding gene and expression vectors from *Thermus oshimai* (Williams R A, et al, 1996, *Int J Syst Bacteriol* 46 (2): 403-408); *Thermus silvanus* and *Thermus chliarophilus* (Tenreiro S, et al., 1995, *Int. J. Syst. Bacteriol* 45 (4): 633-639); *Thermus scotoductus* (Tenreiro S et al., 1995, *Res. Microbiol* 146 (4): 315-324); *Thermus ruber* ATCC 35948, (L. G. Loginova, 1984, *Int. J. Syst. Bacteriol* 34: 498-499); and *Thermus brockianus* (Munster, M. J., 1986, *J. Gen. Microbiol* 132: 1677), which publications are each incorporated herein by reference.

Those of skill in the art will recognize that the above thermostable DNA polymerases with enhanced efficiency for incorporating fluorescein-labeled nucleotides are most easily constructed by recombinant DNA techniques such as site-directed mutagenesis. See for example Sambrook et al., *Molecular Cloning: A Laboratory Manual*, Cold Spring Harbor, 1989, second edition, chapter 15.51, "Oligonucleotide-mediated mutagenesis," which is incorporated herein by reference. This technique is now standard in the art, and can be used to create all possible classes of base pair changes at any determined site in a gene. The method is performed using a synthetic oligonucleotide primer complementary to a single-stranded phage or plasmid DNA to be mutagenized except for a limited mismatching, which represents the desired mutation. Briefly, the synthetic oligonucleotide is used as a primer to direct synthesis of a strand complementary to the phage or plasmid, and the resulting double-stranded DNA is transformed into a phage- or plasmid-supporting host bacterium. The resulting bacteria can be assayed by, for example, DNA sequence analysis or probe hybridization to identify those plaques or colonies carrying the desired mutated gene sequence.

Subsequent to the invention of PCR, primer-directed mutagenesis (described in U.S. Pat. No. 4,683,195, which is herein incorporated by reference) and "overlap PCR" (Higuchi, 1989, in *PCR Technology*, ed. Erlich, Stockton Press, New York, N.Y., pp. 61-70) have become routine means of introducing any mutation at any position of a gene.

The mutated DNA can be recovered from the plasmid, phasmid, phage or amplification reaction by conventional means and ligated into an expression vector for subsequent culture and purification of the resulting enzyme. Numerous cloning and expression vectors are suitable for practicing the invention, including mammalian and bacterial systems, as described in, for example, Sambrook et al., 1989 supra. For convenience, the present invention is exemplified utilizing the lambda derived $P_L$ promoter (Shimatake et al., 1981, *Nature* 292:128). Use of this promotor is specifically described in U.S. Pat. Nos. 4,711,845 and 5,079,352, which are incorporated herein by reference.

Plasmid pCS1 has been deposited with the ATCC, on Aug. 28, 1997, and given accession No. 98521. This plasmid contains a gene encoding a thermostable DNA polymerase which gene is mutated at the codon at position 681 such that glutamic acid is replaced with lysine in the resulting polypeptide and provides a means for providing thermostable DNA polymerases having an enhanced efficiency for incorporating nucleotides labeled with fluorescein family dyes. Example I illustrates the use of flanking restriction sites suitable for subcloning the E681K mutation to create other thermostable DNA polymerase enzymes. Alternatively, because the complete gene sequence for numerous thermostable DNA polymerases are known, other means for introducing the E681K mutation, such as restriction digestion and fragment replacement, are readily available to those of skill in the art, having the availability of ATCC deposits and the sequence information provided herein.

When one desires to produce one of the mutant or native enzymes of the present invention, or a derivative or homologue of those enzymes, the production of the enzyme typically involves the transformation of a host cell with the expression vector, and culture of the transformed host cell under conditions such that expression will occur. Means for transforming and culturing transformed host cells are well known in the art and are described in detail in, for example, Sambrook et al., 1989, supra.

The thermostable DNA polymerases of the present invention are generally purified from *E. coli* strain DG116 (deposited as ATCC 53606 on Apr. 7, 1987) which has been transformed with an expression vector operably linked to a gene encoding a wild-type or modified thermostable DNA polymerase. Methods for purifying the thermostable DNA polymerase are described in, for example, Example I and Lawyer et al., 1993, *PCR Methods and Applications* 2:275-87, which is incorporated herein by reference.

The thermostable enzymes of the invention may be used for any purpose in which such enzyme activity is necessary or desired. Examples of uses include DNA sequencing, DNA labeling, and labeling of primer extension products. DNA sequencing by the Sanger dideoxynucleotide method (Sanger et al, 1977, *Proc. Natl. Acad. Sci.* 74: 5463) is particularly improved by the present invention. Advances in the basic Sanger et al. method have provided novel vectors (Yanisch-Perron et al, 1985 *Gene* 33:103-119) and base analogues (Mills et al., 1979, *Proc. Natl. Acad. Sci.* 76:2232-2235, and Barret al., 1986, *Biotechniques* 4:428-432). In general, DNA sequencing requires template-dependent primer extension in the presence of chain-terminating base analogs, resulting in a distribution of partial fragments which are subsequently separated by size. The basic dideoxy sequencing procedure involves (i) annealing an oligonucleotide primer, optionally labeled, to a template; (ii) extending the primer with DNA polymerase in four separate reactions, each containing a mixture of unlabeled dNTPs and a limiting amount of one chain terminating agent such as a ddNTP, optionally labeled; and (iii) resolving the four sets of reaction products on a high-resolution denaturing polyacrylamide/urea gel. The reaction products can be detected in the gel by autoradiography or by fluorescence detection, depending on the label used, and the image can be examined to infer the nucleotide sequence. These methods utilize DNA polymerase such as the Klenow fragment of *E. coli* Pol I or a modified T7 DNA polymerase.

The availability of thermoresistant polymerases, such as Taq DNA polymerase, resulted in improved methods for sequencing with thermostable DNA polymerase (see Innis et al., 1988, supra) and modifications thereof referred to as "cycle sequencing" (Murray, 1989, *Nuc Acids Res.* 17:8889). As an alternative to basic dideoxy sequencing, cycle sequencing is a linear, asymmetric amplification of target sequences complementary to the template sequence in the presence of chain terminators. A single cycle produces a family of extension products of all possible lengths. Following denaturation of the extension reaction product from the DNA template, multiple cycles of primer annealing and primer extension occur in the presence of terminators such as ddNTPs. Cycle sequencing requires less template DNA than conventional chain-termination sequencing. Thermostable DNA polymerases have several advantages in cycle sequencing; they tolerate the stringent annealing temperatures which are required for specific hybridization of primer to nucleic acid targets as well as tolerating the multiple cycles of high temperature denaturation which occur in each cycle, i.e., 90-95° C. For this reason, AmpliTaq® DNA Polymerase and its derivatives and descendants have been included in Taq cycle sequencing kits commercialized by companies such as Perkin-Elmer, Norwalk, Conn.

Two variations of chain termination sequencing methods exist—dye-primer sequencing and dye-terminator sequencing. In dye-primer sequencing, the ddNTP terminators are unlabeled, and a labeled primer is utilized to detect extension products (Smith et al., 1986, *Nature* 32:674-679). In dye-terminator DNA sequencing, a DNA polymerase is used to incorporate dNTPs and fluorescently labeled ddNTPs onto the end of a DNA primer (Lee et al., supra.). This process offers the advantage of not having to synthesize dye labeled primers. Furthermore, dye-terminator reactions are more convenient in that all four reactions can be performed in the same tube.

Both dye-primer and dye-terminator methods may be automated using an automated sequencing instrument produced by Applied Biosystems, Foster City, Calif. (U.S. Pat. No. 5,171,534, which is herein incorporated by reference). When using the instrument, the completed sequencing reaction mixture is fractionated on a denaturing polyacrylamide gel mounted in the instrument. A laser at the bottom of the instrument detects the fluorescent products as they are electrophoresed according to size through the gel.

Two types of fluorescent dyes are commonly used to label the terminators used for dye-terminator sequencing—negatively charged and zwitterionic fluorescent dyes. Negatively charged fluorescent dyes include those of the fluorescein and BODIPY families. BODIPY dyes (4,4-difluoro-4-bora-3a, 4a-diaza-s-indacene) are described International patent application WO 97/00967, which is incorporated herein by reference. Examples of BODIPY family dyes include BODIPY 503/512 SE (4,4-difluoro-5,7-dimethyl-4-bora-3a, 4a-diaza-s-indacene-3-propionic acid), BODIPY 523/547 (4,4-difluoro-5-phenyl-4-bora-3a,4a-diaza-sindacene-3-propionic acid), BODIPY 530/550 (4,4-difluoro-5,7-diphenyl-4-bora-3a,4a-diaza-sindacene-3-propionic acid), BODIPY 558/568 (4,4 difluoro-5-(2-thienyl)-4-bora-3a,4a-diaza-s-indacene-3-propionic acid), BODIPY 564/570 (4,4-difluoro-5-styryl-4-bora-3a,4a-diaza-s-indacene-3 propionic acid), BODIPY 576/589 (4,4-difluoro-5-(2pyrrolyl)-4-bora-3a,4a-diaza-s-indacene-3-propionic acid), BODIPY 581/591 (4,4-difluoro-5-(4 phenyl-1,3-butadienyl)-4-bora-3a,4a-diaza-s-indacene-3-propionicacid) and BODIPY 589/616 (6-(((4(4, 4-difluoro-5-(2-thienyl)-4bora-3a,4a-diaza-s-indacene-3-yl) phenoxy)acetyl)amino)hexanoic acid).

Zwitterionic fluorescent dyes include those of the rhodamine family. Commercially available cycle sequencing kits use terminators labeled with rhodamine derivatives. However, the rhodamine-labeled terminators are rather costly and the product must be separated from unincorporated dye-ddNTPs before-loading on the gel since they co-migrate with the sequencing products. Rhodamine dye family terminators seem to stabilize hairpin structures in GC-rich regions, which causes the products to migrate anomalously. This requires the use of dITP which relaxes the secondary structure but also affects the efficiency of incorporation of terminator.

In contrast, fluorescein-labeled terminators eliminate the separation step prior to gel loading since they have a greater net negative charge and migrate faster than the sequencing products. In addition, fluorescein-labeled sequencing products have better electrophoretic migration than sequencing products labelled with rhodamine. Although wild-type Taq DNA polymerase does not efficiently incorporate terminators labeled with fluorescein family dyes, this can now be accomplished efficiently by use of the modified enzymes provided herein.

Thus, the scope of this invention includes novel methods for dideoxy sequencing using enzymes having the critical motif, as well as kits for performing the method. In one embodiment, the sequencing method of the invention comprises:
 a) providing a recombinant thermostable DNA polymerase enzyme which is characterized in that
  i) in its native form said polymerase comprises the amino acid sequence LSXXLX(V/I)PXXE (SEQ ID NO: 1), where X is any amino acid,
  ii) the X at position 4 in said sequence is mutated in comparison to said native sequence, except that X is not mutated to E; and
  iii) said thermostable DNA polymerase has reduced discrimination against incorporation of nucleotides labeled with fluorescein family dyes in comparison to the native form of said enzyme; and
 b) performing a dye-terminator sequencing reaction.

In a preferred embodiment of the above method, the native form enzyme has the amino acid sequence LS(Q/G)XL(S/A) IPYEE (SEQ ID NO: 2), where X is any amino acid. In the three-letter code, this amino acid sequence is represented as LeuSerXaaXaaLeuXaaIleProTyrGluGlu (SEQ ID NO: 2), whereby "Xaa" at position 3 is Gln or Gly, "Xaa" at position 4 is any amino acid, and "Xaa" at position 6 is Ser or Ala. In a more preferred embodiment, the native form amino acid sequence is LSQXLAIPYEE (SEQ ID NO:3), where X is any amino acid. In the three-letter code, this amino acid sequence is represented as LeuSerGlnXaaLeuAlaIleProTyrGluGlu (SEQ ID NO:3), whereby "Xaa" at position 4 is any amino acid. In a most preferred embodiment, the "Xaa" at position 4 is Lys.

As described above, DNA sequencing with thermostable DNA polymerases requires a mixture of unconventional base analogues that act as chain-terminators and conventional nucleotides at a specified ratio of concentrations that insures that a population of extension products would be generated representing all possible fragment lengths over a distance of several hundred bases. Some thermostable DNA polymerases previously used for sequencing, such as wild-type Taq polymerase, are characterized in that they preferentially incorporate conventional nucleotides in the presence of a mixture of conventional and unconventional nucleotides. However, some recently described thermostable DNA polymerases allow the ratio of unconventional base analogues to conventional bases to be reduced from a hundred to several hundred fold, or up to over a thousand fold.

One such polymerase is the F667Y mutant of Taq DNA polymerase. Another such mutant is a Taq DNA polymerase having an F667Y mutation and a mutation at position 46 which changes a glycine residue to an aspartic acid residue (G46D) mutation. This mutant polymerase, known as AmpliTaq, FS, is manufactured by Hoffmann-La Roche and marketed by Perkin-Elmer. F730YTma30 DNA Polymerase is another such polymerase. This mutant polymerase is a combination of 1) nucleotides 1-570 of Taq DNA polymerase modified to encode a G46D mutation and 2) nucleotides 571-2679 of Tma DNA polymerase modified to encode an aspartic acid to alanine mutation at position 323, a glutamic acid to alanine mutation at position 325, and a phenylalanine to tyrosine mutation at position 730 (U.S. application Ser. No. 60/05265, which is hereby incorporated by reference). Another polymerase that incorporates unconventional base analogues is a F730Y mutant DNA polymerase from *Thermotoga neapolitana* (International patent applications WO 96/10640, WO 96/41014, and WO 97/09451, which are hereby incorporated by reference). Using these enzymes, for a given dNTP concentration, the rhodamine-ddNTP concentration can be decreased by about 50- to several hundred-fold compared to thermostable DNA polymerases previously available.

The E681K mutation of the invention was combined using recombinant DNA methods with an F667Y mutation to produce the double mutant Taq DNA polymeraseenzyme used in the sequencing reactions described in Example IV. The double mutant was used in a dye-terminator sequencing reaction with fluorescein-labeled dye terminators. The results, described in Example IV, show that the enzyme is capable of incorporating fluorescein-labeled dye terminators in a sequencing reaction and produces sequencing ladders that can be accurately read in an automated sequencing instrument. Unexpectedly, the combination of the E681K and the F667Y mutations was also found to produce a thermostable DNA polymerase enzyme with a 3- to 4-fold increased extension rate relative to an enzyme with the F667Y mutation alone, as measured by the assay described in Example III.

Thus, in another aspect of this invention, the critical motif identified in this invention can be combined with motifs conferring reduced discrimination against ddNTPs to produce polymerases having an increased efficiency of incorporation of both labeled and unlabeled ddNTPs. These polymerases are useful in DNA sequencing methods. In one embodiment of the present invention, a thermostable DNA polymerase having the critical motif defined herein also comprises the critical motif that includes the F667Y mutation, described in U.S. Ser. No 08/448,223. In this embodiment, the thermostable DNA polymerase is characterized in that
  i) in its native form said polymerase comprises a first amino acid sequence LSXXLX(V/I)PXXE (SEQ ID NO: 1), where X is any amino acid,
  ii) the X at position 4 in said first amino acid sequence is mutated in comparison to said native sequence, except that X is not mutated to E; and
  iii) said thermostable DNA polymerase has reduced discrimination against incorporation of nucleotides labeled with fluorescein family dyes in comparison to the native form of said enzyme; and
  iv) said polymerase comprises a second amino acid sequence MRRXXKXXNYXXXYG (SEQ ID NO: 12) where X is any amino acid;
  v) said thermostable DNA polymerase also has reduced discrimination against incorporation of unconventional nucleotides in comparison to the native form of said enzyme. In the three-letter code, the second amino acid sequence is represented by MetArgArgXaaXaaLysXaaXaaAsnTyrXaaXaaXaaTyrGly (SEQ ID NO: 12), where "Xaa" at positions 4, 5, 7, 8, 11, 12, and 13 is any amino acid. In a preferred embodiment, the "Xaa" at position 4 in the first amino acid sequence is mutated to Lys. In a more preferred embodiment, the enzyme is Taq DNA polymerase and it comprises the E681K and F667Y mutations. Also within the scope of this invention are methods of sequencing using the above polymerases.

Also within the scope of this invention is the improved sequencing method of the invention performed using thermostable DNA polymerase enzymes having a critical motif which is not derived by mutation, but which critical motif exists as a natural variant. In this aspect, the DNA polymerase of a thermophilic bacterial species has a critical motif in which the residue at position 4 is not Glu. For example, in the thermostable DNA polymerase from *Thermotoga neapolitana*, the X at position 4 in the motif LSXXLX(V/I)PXXE (SEQ ID NO: 7), where X is any amino acid except E, is an arginine residue. Thus, the invention provides for improved methods of DNA sequencing using a native thermostable DNA polymerase which comprises the amino acid sequence LSXXLX(V/I)PXXE (SEQ ID NO: 7) where X can be any amino acid except E. In the three-letter code, this amino acid sequence is represented as LeuSerXaaXaaLeuXaaXaaProXaaXaaGlu (SEQ ID NO: 7), where "Xaa" at positions 3, 6, 9, and 10 are any amino acid and "Xaa" at position 4 is any amino acid except Glu and "Xaa" at position 7 is Val or Ile. In this embodiment, the sequencing method of the invention comprises:
  a) providing a thermostable DNA polymerase which is characterized in that
    i) said polymerase comprises the amino acid sequence LSXXLX(V/I)PXXE (SEQ ID NO: 7), where X at position 4 is any amino acid except E,
    ii) said thermostable DNA polymerase has reduced discrimination against incorporation of nucleotides labeled with fluorescein family dyes; and
  b) providing a dye-terminator labeled with a fluorescein family dye, and
  c) performing a dye-terminator sequencing reaction.

In a more preferred embodiment, the sequencing method of the invention comprises:
  a) providing a thermostable DNA polymerase which is characterized in that
    i) said polymerase comprises a first amino acid sequence LSXXLX(V/I)PXXE (SEQ ID NO: 7), where X at position 4 is any amino acid except E,
    ii) said thermostable DNA polymerase has reduced discrimination against incorporation of nucleotides labeled with fluorescein family dyes;
    iii) said polymerase comprises a second amino acid sequence MRRXXKXXNYXXXYG (SEQ ID NO: 12) where X is any amino acid.
    iv) said thermostable DNA polymerase has reduced discrimination against incorporation of unconventional nucleotides; and
  b) providing a dye-terminator labeled with a fluorescein family dye, and
  c) performing a dye-terminator sequencing reaction.

In another preferred embodiment, the enzyme comprises the amino acid sequence LS(Q/G)XL(S/A)IPYEE (SEQ ID NO: 13), where X at position 4 is any amino acid except E. In the three-letter code, this amino acid sequence is represented as LeuSerXaaXaaLeuXaaIleProTyrGluGlu (SEQ ID NO: 13) whereby "Xaa" at position 3 is Gln or Gly, "Xaa" at position 4 is any amino acid except Glu, and "Xaa" at position 6 is Ser or Ala. In a more preferred embodiment, the amino acid sequence is LSQXLAIPYEE (SEQ ID NO:14), where X is any amino acid except E. In the three-letter code, this amino acid sequence is represented as LeuSerGlnXaaLeuAlaIleProTyrGluGlu (SEQ ID NO: 14), whereby "Xaa" at position 4 is any amino acid except Glu.

In yet another preferred embodiment, the enzyme has the amino acid sequence LSVXLG(V/I)PVKE (SEQ ID NO: 15), where X is any amino acid except E. In the three-letter code, this amino acid sequence is represented as LeuSerValXaaLeuGlyXaaProValLysGlu (SEQ ID NO: 15), whereby "Xaa" at position 4 is any amino acid except Glu and "Xaa" at position 7 is Val or Ile. In a more preferred embodiment, the amino acid sequence is LSVXLGVPVKE (SEQ ID NO: 16), where X is any amino acid except E. In the three-letter code, this amino acid sequence is represented as LeuSerValXaaLeuGlyValProValLysGlu (SEQ ID NO: 16), whereby "Xaa" at position 4 is any amino acid except Glu. In a most preferred embodiment, the "Xaa" at position 4 is Arg. In another more preferred embodiment, the amino acid sequence is LSVXLGIPVKE (SEQ ID NO: 17), where X is any amino acid except E. In the three-letter code, this amino acid sequence is represented as LeuSerValXaaLeuGlyIleProValLysGlu (SEQ ID NO: 17), whereby "Xaa" at position 4 is any amino acid except Glu. In a most preferred embodiment, the "Xaa" at position 4 is Arg.

In another embodiment of the invention, the sequencing methods are performed using a native enzyme which has a reduced level of discrimination against nucleotide labeled with fluorescein family dyes which level is measured using a ddNTP incorporation assay such as that described in Example II. The concentration of ddCTP required for 50% inhibition of DNA synthesis is determined, as is the concentration of Zowie-ddCTP needed for 50% inhibition. The ratio of the concentration for Zowie-ddCTP to the concentration for ddCTP is calculated. In a preferred embodiment, the ratio is 10 or less. In a more preferred embodiment, the ratio is 4 or less. In a most preferred embodiment, the ratio is 1.2 or less.

Although the examples provided herein use dideoxynucleotides labeled with fluorescein family dyes, the use of other unconventional nucleotides and fluorescent dyes is also within the scope of this invention. Other unconventional nucleotides include fluorescently-labled dNTPs, which can be used to label the products of DNA synthesis, and fluorescently-labled rNTPs, which can be used to label the primer extension products. Other dyes include other negatively charged fluorescent dyes, such as BODIPY, which are structurally and chemically similar to fluorescein. Other dyes also include cyanine dyes. Cyanine-labeled dNTPs were added to a standard PCR reaction which included a Taq DNA polymerase with the E68 I K mutation (and a G46D mutation). The cyanine-labeled dNTPs were unexpectedly found to be incorporated into amplification products at a level that was higher than for the wild-type enzyme. Thus, in this aspect, a method of labeling DNA of the invention uses a native or mutant polymerase of the invention in combination with a nucleotide labeled with either a negatively charged fluorescent dye or a cyanine dye. In one embodiment, the DNA labeling method of the invention comprises:

a) providing a thermostable DNA polymerase characterized in that
  i) said polymerase comprises the amino acid sequence LSXXLX(V/I)PXXE (SEQ ID NO: 7) where X at position 4 can be any amino acid except E
  ii) said polymerase has reduced discrimination against incorporation of unconventional nucleotides, and
b) providing a nucleotide labeled with a negatively charged fluorescent dye, and
c) performing a DNA synthesis reaction.

In another embodiment, the DNA labeling method of the invention comprises:

a) providing a thermostable DNA polymerase characterized in that
  i) said polymerase comprises the amino acid sequence LSXXLX(V/I)PXXE (SEQ ID NO: 7) where X at position 4 can be any amino acid except E
  ii) said polymerase has reduced discrimination against incorporation of unconventional nucleotides, and
b) providing a nucleotide labeled with a cyanine dye, and
c) performing a DNA synthesis reaction.

In another aspect of the invention, a thermostable DNA polymerase is provided which combines a mutation allowing more efficient incorporation of rNTPs, such as the glutamic acid to glycine mutation at position 615 of Taq DNA polymerase, and the critical motif of this invention. The resulting enzyme is expected to have an increased efficiency of incorporation of ribonucleotides labeled with fluorescein family dyes. Thus, in one embodiment, the invention provides a recombinant thermostable DNA polymerase which (1) in its native form comprises the amino acid sequence LSXXLX(V/I)PXXE (SEQ ID NO: 1) where X is any amino acid and (2) the X at position 4 is mutated such that X at position 4 is not mutated to E and (3) also comprises the region of criticality which is amino acid sequence SQIXLR(V/I) (SEQ ID NO: 18) where "X" is any amino acid except E, and (4) is capable of efficient incorporation of ribonucleotides labeled with fluorescein family dyes. In the three-letter code, the latter sequence is represented as SerGlnIleXaaLeuArgXaa, where "Xaa" at position 4 is any amino acid except Glu and "Xaa" at position 7 is Val or Ile Mutant polymerase domains such as that for Taq containing the E615G and E681K mutations are useful in improved methods of producing primer extension products labeled with fluorescein family dyes. For example, in a primer extension reaction such as PCR, rNTPs labeled with fluorescein family dyes are substituted at least partially for one of the 4 standard dNTPs and a double mutantpolymerase such as E681K E615G Taq DNA polymerase is included. The mutant polymerase synthesizes primer extension products that have fluorescein-labeled ribonucleotide residues at various positions along their lengths. Upon heat or alkali treatment, the primer extension products are fragmented at each ribonucleotide residue, producing a population of end-labeled fragments. This population of uniformly labeled fragments represents a distribution of the fluorescent label across the length of the primer extension product. Labeled fragments of these characteristics are useful in nucleic acid detection formats based dn silicon chips, such as that of (Cronin et al., supra.). Thus, in one embodiment, the invention provides a method of labeling primer extension products which comprises (1) providing a thermostable DNA polymerase which (a) in its native form comprises the amino acid sequence LSXXLX(V/I)PXXE (SEQ ID NO: 1) where X is any amino acid, (b) the X at position 4 is mutated such that X at position 4 is not mutated to E, (c) also comprises the region of criticality which is amino acid sequence SQIXLR(V/I) (SEQ ID NO: 18) where "X" is any amino acid except E and (d) is capable of efficient incorporation of ribonucleotides labeled with fluorescein and/or cyanine family dyes, and (2) performing a primer extension reaction.

In yet another aspect, enzymes having the critical motif of this invention display an increased rate of extension relative to the wild-type enzyme as shown in Example IV for a E681 K F667Y mutant. In one embodiment, the enzyme is characterized in that (I) in its native form, it comprises the amino acid sequence LSXXLX(V/I)PXXE (SEQ ID NO: 1) where X is any amino acid, (2) the amino acid sequence is mutated at position 4 such that X at position 4 is not mutated to E, and (3) it has an increased extension rate relative to the wild-type enzyme. In a preferred embodiment, the enzyme is characterized in that (1) in its native form, it comprises the amino acid sequence LSXXLX(V/I)PXXE (SEQ ID NO: 1) where X is any amino acid, (2) the amino acid sequence is mutated at position 4 such that X at position 4 is not mutated to E and (3) it also comprises the amino acid sequence MRRXXKXX-NYXXXYG (SEQ ID NO: 12) where X is any amino acid and (4) has an increased extension rate. In a more preferred embodiment, the enzyme is characterized in that (1) in its native form it contains the amino acid sequence LSXXLX(V/I)PXXE (SEQ ID NO: 1) where X is any amino acid and (2) the amino acid sequence is mutated at position 4 such that X at position 4 is mutated to K. In a most preferred embodiment, the enzyme is Taq DNA polymerase and contains the E681K mutation and the F667Y mutation. Also included within this aspect are methods of sequencing and labeling of DNA using the polymerases with increased extension rate as well as kits for doing the same.

In a preferred method for DNA sequencing according to the invention, thermostable pyrophosphatase is included in the reaction mixture. Pyrophosphatase has been shown to enhance sequencing data using mesophilic as well as the mutant thermostable DNA polymerases described in U.S. Ser. No. 08/528,384.

In an exemplified embodiment, the thermostable DNA polymerase of the invention also contains a mutation in the 5'-nuclease domain that serves to greatly attenuate this nuclease activity. Modified forms of Taq polymerase have been described in PCT Patent Publication No. WO 92/06200, published Apr. 16, 1992 and in U.S. Pat. No. 5,466,591. In one embodiment of that invention, the codon for the glycine residue at amino acid position 46 has been replaced with a codon for aspartic acid (G46D mutation). The resulting enzyme has enhanced utility in cycle sequencing reactions due to the decreased 5'-nuclease activity. The polymerase domain amino acid sequence and polymerase activity are both unchanged in the G46D mutant in comparison to the wild-type enzyme.

In a commercial embodiment of the invention, kits for practicing methods that are improved by use of the present invention are considered to be an additional aspect of the invention. One such kit for DNA sequencing comprises
   a) a thermostable DNA polymerase characterized in that
      i) said polymerase comprises the amino acid sequence LSXXLX(V/I)PXXE (SEQ ID NO: 7) where X at position 4 can be any amino acid except E
      ii) said polymerase has reduced discrimination against incorporation of nucleotides labeled with fluorescein family dyes, and
   b) a dye-terminator labeled with a negatively charged fluorescent dye and may additionally include other reagents for DNA sequencing such as dNTPs, thermostable pyrophosphatase and appropriate buffers. In another embodiment, the enzyme in the kit has the amino acid sequence LSVXLG(V/I)PVKE (SEQ ID NO: 15), whereby X is any amino acid except E. In the three-letter code, this amino acid sequence is represented as LeuSerValXaaLeuGlyXaaProValLysGlu (SEQ ID NO: 15), whereby "Xaa" at position 4 is any amino acid except Glu and "Xaa" at position 7 is Val or Ile. In a preferred embodiment, the amino acid sequence is LSVXLGVPVKE (SEQ ID NO: 16), where X is any amino acid except E. In the three-letter code, this amino acid sequence is represented as LeuSerValXaaLeuGlyValProValLysGlu (SEQ ID NO: 16), whereby "Xaa" at position 4 is any amino acid except E. In a more preferred embodiment, the "Xaa" at position 4 is Arg. In another preferred embodiment, the amino acid sequence is LSVXLGIPVKE (SEQ ID NO: 17) where X is any amino acid except E. In the three-letter code, this amino acid sequence is represented as LeuSerValXaaLeuGlyIleProValLysGlu (SEQ ID NO: 17), whereby "Xaa" at position 4 is any amino acid except Glu. In a more preferred embodiment, the "Xaa" at position 4 is Arg.

Other kits for DNA sequencing comprise a mutant thermostable DNA polymerase characterized in that
   a) in its native form said polymerase comprises the amino acid sequence LSXXLX(V/I)PXXE (SEQ ID NO: 1) where X is any amino acid,
   b) said amino acid sequence is mutated at position 4, except that X at position 4 is not mutated to E; and
   c) said thermostable DNA polymerase has reduced discrimination against incorporation of nucleotides labeled with fluorescein family dyes in comparison to the native form of said enzyme and may additionally include reagents for DNA sequencing such as chain terminating compounds, dNTPs, thermostable pyrophosphatase and appropriate buffers. Where the terminators are labeled, preferable labels are fluorescent dyes, more preferable labels are negatively charged fluorescent dyes or cyanine dyes, and the most preferable labels are fluorescein family dyes. In a preferred embodiment, the enzyme in the kit has the amino acid sequence LS(Q/G)XL(S/A)IPYEE (SEQ ID NO: 2), where X is any amino acid. In the three-letter code, this amino acid sequence is represented as LeuSerXaaXaaLeuXaaIleProTyrGluGlu (SEQ ID NO: 2), whereby "Xaa" at position 3 is Gln or Gly, "Xaa" at position 4 is any amino acid, and "Xaa" at position 6 is Ser or Ala. In a more preferred embodiment, the amino acid sequence is LSQXLAIPYEE (SEQ ID NO:3), where X is any amino acid. In the three-letter code, this amino acid sequence is represented as LeuSerGlnXaaLeuAlaIleProTyrGluGlu (SEQ ID NO:3), whereby "Xaa" at position 4 is any amino acid. In a most preferred embodiment, the "Xaa" at position 4 is Lys.

Kits for labeling DNA comprise a thermostable DNA polymerase which is characterized in that (a) in its native form, the polymerase comprises the amino acid sequence LSXXLX(V/I)PXXE (SEQ ID NO: 1) where X is any amino acid, (b) the X at position 4 in said sequence is mutated in comparison to said native form, except that X at position 4 is not mutated to E, and c) the enzyme has reduced discrimination against incorporation of nucleotides labeled with fluorescein family dyes, in comparison to the corresponding wild-type enzyme and may additionally include dNTPs and appropriate buffers. In a preferred embodiment, the X at position 4 is mutated to K. Other kits for producing labeled DNA comprise a) a nucleotide or nucleotide analog labeled with a negatively charged fluorescent compound and b) a native thermostable DNA polymerases having the following critical motif:
   LSXXLX(V/I)PXXE (SEQ ID NO: 7)

where X at position 4 can be any amino acid except E and said polymerase has reduced discrimination against incorporation of fluorescein-labeled nucleotides, and may additionally include dNTPs and appropriate buffers. In a preferred embodiment, the X at position 4 is K. In another preferred embodiment, the X at position 4 is R.

Kits for labeling primer extension products comprise a thermostable DNA polymerase which is characterized in that (a) in its native form, the polymerase comprises the amino acid sequence LSXXLX(V/I)PXXE (SEQ ID NO: 1) where X is any amino acid, (b) the X at position 4 in said sequence is mutated in comparison to said native sequence, except that X at position 4 is not mutated to E, c) the polymerase also comprises the second amino acid sequence SQIXLR(V/I) (SEQ ID NO: 18) where "X" is any amino acid except E, d) the enzyme has reduced discrimination against incorporation of ribonucleotides labeled with fluorescein family dyes, in comparison to the corresponding wild-type enzyme, and may additionally include a ribonucleotide or ribonucleotide analog labeled with a negatively charged fluorescent compound or cyanine compound, dNTPs, and appropriate buffers. In a preferred embodiment, the polymerase contains a E681K mutation and a E615G mutation. Other kits for producing labeled primer extension products comprise a) a ribonucleotide or ribonucleotide analog labeled with a negatively charged fluorescent compound or cyanine compound and b) a native thermostable DNA polymerase characterized in that it (i) comprises the critical motif which is the amino acid sequence:
   LSXXLX(V/I)PXXE (SEQ ID NO: 7)

where X at position 4 can be any amino acid except E, (ii) comprises the second amino acid sequence SQIXLR(V/I) where "X" is any amino acid except E, and (iii) has reduced discrimination against incorporation of fluorescein-labeled ribonucleotides, and may additionally include dNTPs and appropriate buffers. In a preferred embodiment, in the first amino acid sequence, the X at position 4 is a K and in the second amino acid sequence, the X is a G. In another preferred embodiment, in the first amino acid sequence, the X at position 4 is a R and in the second amino acid sequence, the X is a G.

The following examples are offered by way of illustration only and are by no means intended to limit the scope of the claimed invention.

EXAMPLE I

Expression of a Modified Taq Polymerase Gene Having Reduced Discrimination Against Nucleotides Labeled with Fluorescein Family Dyes The C-terminal amino acid portion of Taq DNA polymerase encodes the polymerase active site domain (Lawyer et al., 1993, *PCR Methods and Applications* 2:275-287, Freemont et al., 1986, *Proteins: Structure, Function and Genetics* 1:66-73, which are incorporated herein by reference). A DNA fragment containing this region was isolated from the full-length Taq gene and mutagenized by PCR amplification in the presence of manganese (Leung et al, 1989, *Technique* 1(1): 11-15). For this example, all restriction enzymes were purchased from New England Biolabs, Beverly Mass. The mutagenized fragments were digested with PstI and BglII and cloned into a Taq expression plasmid, pLK102, which had been digested with PstI and BglII. Plasmid pLK102 is a derivative of pLK101 in which the 900 bp PstI-BglII fragment is replaced by a short PstI-BglII linker. Plasmid pLK101 is a modified form of pSYC1578 (Lawyer et al., 1993, supra and U.S. Pat. No. 5,079,352), in which the small HincII/EcoRV fragment located 3' to the polymerase coding region was deleted.

The resulting expression plasmids were transformed into *E. coli* strain N1624 (available from the *E. coli* Genetic Stock Center at Yale University, strain No. CGSC #5066) and the resulting transformants were screened for the ability to more efficiently incorporate [$\alpha$-$^{32}$P]Tet-dCTP in comparison to the wild-type enzyme. Using this procedure Mutant CS1, was identified as having the ability to more efficiently incorporate [$\alpha$-$^{32}$P]Tet-dCTP. The mutagenized Taq expression plasmid of mutant CS1 was digested with HindIII/NheI and the resulting restriction fragment was subcloned into the wild-type gene of pLK101, replacing the unmutagenized HindIII/NheI fragment, to determine which portion of the mutagenized Taq polymerase gene was responsible for the altered phenotype. Subclones containing the HindIII/NheI restriction fragment conferred the altered phenotype on the wild-type enzyme, indicating that the mutation was within this fragment. Subsequent subclone analysis determined that the mutation was located in the 265 bp BamHI-NheI fragment.

DNA sequence analysis of the 265 NheI-BamHI fragment was performed on pCS1 using the TaqFS DyeDeoxy™ Terminator Cycle Sequencing Kit from Applied Biosystems, Foster City, Calif., and the Applied Biosystems Model Prism 377 DNA Sequencing System. The sequence analysis identified a missense mutation in the Taq polymerase gene at amino acid position 681, that caused a Glutamic acid (E) residue to be replaced by a Lysine (K) residue. Numbering is initiated at the codon encoding the first methionine residue of the mature protein, as in U.S. Pat. No. 5,079,352, which is herein incorporated by reference. This mutation, E681K, specifically was caused by a GAG to AAG change in the codon sequence. Plasmid pCS1 was deposited with the ATCC on Aug. 28, 1997, and given accession No. 98521.

Plasmid pCS1 may contain additional mutations in the coding sequence for Taq polymerase; however, by further subcloning experiments, the E681K mutation was determined to be solely responsible for the increased efficiency in incorporation of nucleoside triphosphates labeled with fluorescein dyes. This point mutation is located in the 265 base pair BamHI-NheI DNA fragment shown in FIG. 1. Within the 265 bp DNA fragment, the E681K mutation is the only change from the wild-type Taq polymerase gene sequence.

For further analysis and quantitation of the efficiency of incorporation of nucleotide analogues, the 265 bp BamHI-NheI fragment of plasmid pCS1 was cloned into a Taq expression vector that contained the wild-type sequence within the polymerase domain, pRDA3-2. Plasmid pRDA3-2 referred to as clone 3-2, is fully described in PCT Patent Publication No. WO 92/06200, which is incorporated herein by reference. A second clone encoding both the E681K mutation as well as a F667Y mutation was created by primer-directed mutagenesis and subsequent cloning of a PCR product containing both mutations into the BamHI-NheI sites of plasmid pRDA3-2.

Expression vector pRDA3-2 contains the full-length Taq DNA polymerase gene operably linked to the phage lambda P$_L$ promoter. In vector pRDA3-2, the 5'-nuclease domain of the Taq DNA polymerase gene contains a point mutation at the codon encoding glycine at position 46 that reduces 5'-nuclease activity (G46D mutation). However, the gene sequence within the polymerase domain of the expression vector pRDA3-2 is identical to the wild-type Taq DNA polymerase gene sequence. Plasmids, pRDA3-2, pCS1 and the E681K F667Y PCR product were digested with BamHI and NheI and the 265 bp DNA fragment from plasmid pCS1 or the PCR product was ligated into vector pRDA3-2 by conventional means. The resulting plasmids, pLK112 and pLK113, respectively, were transformed into *E. coli* strain DG116 (ATCC No. 53606). These plasmids encode thermostable DNA polymerases herein referred to as G46D E681K Taq and G46D E681K F667Y Taq, respectively. The expressed thermostable DNA polymerase protein G46D E681K F667Y Taq was purified according to the method described by Lawyer et al., 1993, supra.

The G46D E681K Taq enzyme was purified using a similar, but smaller scale preparation method as follows: All steps were preformed at 4° C. unless indicated otherwise. Cells from a 475 ml culture were resuspended in 30 ml of buffer (50 mM Tris-HCl, pH 7.5, 10 mM EDTA, pH 8.0, 0.5 mM Pefabloc©SC, 0.5 µg/ml leupeptin, 0.1 mM N$\alpha$-p-tosyl-L-Lysine Chloromethyl Ketone, 1 mM DTT). Cells were sonicated at 50% duty cycle, setting 5 for 1 minute, and cooled on ice for 1 minute. This step was repeated twice more. Then 1.5 ml of 4.0 M ammonium sulfate was added and the mixture heated in a 75° C. water bath for 15 minutes, followed by cooling on ice. Polyethyleneimine was added to 0.6% and the mixture was incubated on ice for 10 minutes. The mixture was centrifuged at 16,000×g for 30 minutes. The supernatant was loaded on a 1.8 ml volume phenyl-sepharose column (Bio-rad Polyprep chromatography column) equilibrated with a solution of 50 mM Tris-HCl, pH 7.5, 10 mM EDTA, pH 8.0, 1 mM DTT, 0.2 M (NH$_4$)$_2$SO$_4$. The column was washed with 6 ml. each of three solutions: 1) 25 mM Tris-HCl, pH 7.5, 1 mM EDTA, 1 mM DTT, 0.2 M (NH$_4$)$_2$SO$_4$, 2) 25 mM Tris-HCl, pH 7.5, 1 mM EDTA, 1 mM DTT, and 3) 25 mM Tris-HCl, pH 7.5, 1 mM EDTA, 1 mM DTT, 20% ethylene glycol. The polymerase was eluted with 6 ml of 25 mM Tris-HCl, pH 7.5, 1 mM EDTA, 1 mM DTT, 20% ethylene glycol, 2.5 M urea. After adjusting the polymerase preparation to 100 mM KCl with 3M KCl, the mixture was loaded on a heparin-sepharose column (1.8 ml volume, Bio-rad Poly-prep column) equilibrated in 25 mM Tris-HCl, pH 7.5, 1 mM EDTA, 1 mM DTT, 100 mM KCl. After a wash with the same buffer, the sample was eluted in a buffer of 25 mM Tris-HCl, pH 7.5, 1 mM EDTA, 1 mM DTT, 400 mM KCl.

Following purification, the activity of the modified enzymes was determined by the activity assay described in Lawyer et al., 1989, *J. Biol. Chem.* 264:6427-6437, which is incorporated herein by reference. The activity of the purified enzymes was calculated as follows: one unit of enzyme corresponds to 10 nmoles of product synthesized in 30 min. DNA polymerase activity is linearly proportional to enzyme concentration up to 80-100 pmoles dCMP incorporated (diluted enzyme at 0.024-0.03 units/µl). The purified enzymes were utilized in the incorporation and sequencing reactions described in Examples II-IV.

EXAMPLE II

Assay to Compare Efficiency of Incorporation of ddNTPs

The relative abilities of G46D F667Y Taq, G46D F667Y E681K Taq and F730Y Tma30 DNA polymerases to incorporate a fluorescein dye family-labeled ddCTP were compared by use of a limiting template, primer extension competition assay. F730Y Tma30 DNA polymerase is described in Example I of U.S. Ser. No. 60/05265, filed Jul. 6, 1997, and is herein incorporated by reference. In this competition assay, because the incorporation of a ddCTP terminates the extension reaction, the more readily the polymerase incorporates a ddCTP into an extended primer, the less [$\alpha$-$^{33}$P]dCTP can be incorporated. Thus, as the efficiency of ddCTP incorporation increases, the extent of inhibition of DNA synthesis is increased. The efficiency of incorporation of ddCTP is then compared to the efficiency of incorporation of fluorescently labeled ddCTP to give a relative measurement of the efficiency of incorporation of fluorescently-labeled ddNTPs for a given enzyme.

The assay was performed as previously described (Lawyer et al., 1989, *J. Biol. Chem.* 264:6427) including the following modifications. The assay mixture was composed so the final concentration was 50 mM Bicine pH 8.3, 25° C., 2.5 mM MgCl$_2$, 1 mM β-mercaptoethanol, 20 µM each of dATP, dGTP and dTTP (Perkin-Elmer), 20 µM dCTP (Perkin-Elmer) and [$\alpha$-$^{33}$P]dCTP (New England Nuclear, Boston, Mass.). M13 mp18 (Perkin-Elmer) was annealed to primer DG48, (SEQ ID NO: 10) and the equivalent of 0.085 pmoles of the annealed template was added to the assay mixture for each reaction. Thirty-five µl of the assay mixture with template DNA was added to each of 38 0.5 ml eppendorf tubes. Dilutions of Zowie-ddCTP in 25 mM CAPSO buffer, pH 9.6 were prepared such that when 10 µl of each was added to the reaction tube, the final concentration of Zowie-ddCTP would be 3, 1, 0.5, 0.25, 0.125, or 0.0625 µM. For G46D F667Y Taq DNA polymerase, two tubes each of the 3, 1, 0.5, 0.25, 0.125 µM Zowie-ddCTP were prepared. For G46D F667Y E681K Taq and F730Y Tma30 DNA polymerases, two tubes each of the 1, 0.5, 0.25, 0.125, and 0.0625 µM Zowie-ddCTP were prepared. The eight remaining reaction tubes received 10 µl of 25 mM CAPSO buffer, pH 9.6. Thus, each of the thirty-eight tubes contained 35 µl of assay mix and 10 µl of either 25 mM CAPSO buffer, pH 9.6 or one of the Zowie-ddCTP dilutions.

For each enzyme to be tested, polymerization was initiated in one tube of each Zowie-ddCTP dilution and two tubes containing the CAPSO buffer alone using 5 µl of the enzyme. The following concentrations of the enzymes were used, each predetermined to be an excess amount of enzyme for the amount of substrate in the assay: 2.5 units of F667Y G46D Taq DNA polymerase prepared as in Example I; 1.25 units of G46D, F667Y, E681K Taq DNA polymerase, prepared as in Example I; or 2 units of F730Y Tma30 DNA polymerase. As a control for the level of background, the remaining negative control was initiated with enzyme dilution buffer rather than polymerase. All reaction tubes were immediately vortexed briefly and incubated for 10 minutes at 750 C. The reactions were stopped by addition of 10 µl 60 mM EDTA and stored at 0° C.

In an analogous experiment, ddCTP was diluted in 25 mM CAPSO buffer, pH 9.6 such that when 10 µl of each dilution was added to the reaction tubes, the final concentration would be 0.5, 0.25, 0.125, 0.0625, or 0.0312 µM. Ten µl of each dilution was pipetted into each of three 0.5 ml Eppendorf tubes containing 35 µl of the assay mixture as described above. Four tubes containing 35 µl of the assay mix plus 10 µl of 25 mM CAPSO buffer, pH 9.6 were also prepared. Thus, each of the 19 tubes contained 35 µl of assay mix and 10 µl each of either 25 mM CAPSO, pH 9.6 or one of the ddCTP dilutions.

Polymerization was initiated in one tube of each ddCTP dilution and one tube of CAPSO buffer with 2.5 units of G46D F667Y Taq DNA polymerase, 1.25 units of G46D F667Y E681K Taq DNA polymerase or 2 units of F730Y Tma30 DNA polymerase. The remaining tube containing CAPSO was initiated with enzyme dilution buffer rather than the polymerase-containing buffer as a negative control. All reactions were immediately vortexed and incubated 10 minutes at 75° C. The reactions were stopped by addition of 10 microliters of 60 mM EDTA and stored at 0° C.

For each reaction, a 50 µl aliquot of the 60 µl reaction was diluted with 1 ml 2 mM EDTA, 50 µg/ml sheared salmon sperm DNA as a carrier. The DNA was precipitated with TCA using standard procedures and collected on GF/C filter discs (Whatman). The amount of incorporated [$\alpha$-$^{33}$P]dCMP was determined for each sample and normalized to the CAPSO samples without ddNTP (0% inhibition). The concentration of ddCTP or Zowie-ddCTP needed for 50% inhibition was calculated for each sample and is shown in Table 2. Comparison of the amount of ddCTP needed to inhibit synthesis 50% with the amount of Zowie-ddCTP required to inhibit synthesis by 50% for a particular enzyme reflects the relative ability of each enzyme to incorporate fluorescently-labeled analog. These data show that G46D F667Y Taq DNA polymerase incorporates Zowie-ddCTP least efficiently of the three enzymes tested (ratio of concentrations for 50% inhibition by Zowie-ddCTP vs. ddCTP=25). F730Y Tma30 DNA polymerase incorporates this labeled analog more efficiently than G46D F667Y Taq DNA polymerase (ratio of concentrations for 50% inhibition by Zowie-ddCTP vs. ddCTP =4), while G46D F667Y E681K Taq DNA polymerase incorporates labeled and unlabeled ddCTP with nearly equal efficiency (ratio of concentrations for 50% inhibition by Zowie-ddCTP vs. ddCTP=1.2).

TABLE 2

| | Concentration (µM) of Zowie-ddCTP or ddCTP needed for 50% inhibition | | |
|---|---|---|---|
| DNA polymerase | Zowie-ddCTP | ddCTP | Zowie-ddCTP/ddCTP |
| G46D F667Y Taq | 1.4 | 0.056 | 25 |
| G46D F667Y E681K Taq | 0.14 | 0.116 | 1.2 |
| F730Y Tma30 | 0.236 | 0.057 | 4 |

EXAMPLE III

Extension Rate Assay

The extension rate of G46D F667Y Taq and G46D F667Y E681K Taq were determined using an extension rate assay. In this experiment, the enzymes were used to extend a primer annealed to an M13 template in the presence of [$\alpha$-$^{33}$P]dCTP. The extension reactions were denatured and the products analyzed by denaturing agarose gel electrophoresis.

The assay was performed as previously described (Lawyer et al., 1989, *J. Biol. Chem.* 264:6427) including the following modifications. The assay mixture was composed so the final concentration was 50 mM Bicine pH 8.3, 25° C., 2.5 mM MgCl$_2$, 1 mM β-mercaptoethanol, 200 µM each of dATP, dGTP and dTTP (Perkin-Elmer), 100 µM dCTP (Perkin-Elmer) containing [α-$^{33}$P]dCTP (New England Nuclear, Boston, Mass.). M13 mp18 (Perkin-Elmer) was annealed to primer DG48, (SEQ ID NO: 11), and the equivalent of 0.085 pmoles of the annealed template was added to the assay mixture for each reaction. Forty-five µl of the assay mixture with template DNA was added to each of fourteen 0.5 ml eppendorf tubes. Each tube was preincubated at 75° C. for at least 30 seconds before the start of the polymerase reaction.

Polymerization was initiated in six of the fourteen assay tubes with 5 µl of G46D F667Y Taq DNA polymerase (2.5 units) or G46D F667Y E681K Taq DNA polymerase (1.25 units). Both enzymes were prepared as in Example I and the concentration used represents a predetermined excess amount of enzyme for the amount of substrate in the assay. As a control for the level of background, the remaining negative control was initiated with enzyme dilution buffer rather than polymerase. All reaction tubes were immediately vortexed briefly and incubated at 75° C. Two of the six tubes containing G46D F667Y Taq DNA polymerase were incubated 3 minutes, two for 6 minutes and two for 10 minutes. Similarly, two of the tubes started with G46D F667Y E681K Taq DNA polymerase were incubated for 30 seconds, two for 1 minute and two for 2 minutes. The control tubes were incubated for 3 minutes. The reactions were stopped by addition of 10 µl 60 mM EDTA and stored at 0° C.

For each reaction, a 25 µl aliquot of the 60 µl reaction was diluted with 1 ml 2 mM EDTA, 50 µg/ml sheared salmon sperm DNA as a carrier. The DNA was precipitated with TCA using standard procedures and collected on GF/C filter discs (Whatman). The amount of incorporated [α-$^{33}$P]dCMP was determined for each sample.

The remaining 35 µl of each duplicated were combined and the 70 µl sample was ethanol precipitated, dried and resuspended in 50 mM NaOH, 1 mM EDTA. Aliquots were removed from these samples such that an equal number of α-$^{33}$P] counts were taken from each. These aliquots were loaded on an 0.9% alkaline agarose gel, electrophoresed, dried and autoradiographed as previously described (Maniatis et al., 1982, In *Molecular Cloning: A Laboratory Manual*, Cold Spring Harbor Laboratory, Cold Spring Harbor, N.Y.) Bacteriophage lambda DNA cut with restriction enzyme HindIII (BRL) and 5' end-labeled with [$^{32}$P] was used as a molecular weight standard.

The length in base pairs of the extension product in each sample was determined by comparison of the migration distance of each sample with the distance migrated by the lambda DNA size standard. The number of base pairs in each product was divided by the number of seconds each extension reaction incubated to give the extension rate as shown below.

| DNA Polymerase | Time | Base Pairs/Sec |
| --- | --- | --- |
| G46D F667Y Taq | 3 min. | 12.5 |
| G46D F667Y Taq | 6 min. | 12.2 |
| G46D F667Y Taq | 10 min. | 11.8 |
| G46D F667Y E681K Taq | 30 sec. | 36.7 |
| G46D F667Y E681K Taq | 1 min. | 41.7 |
| G46D F667Y E681K Taq | 2 min | 52.9 |

These results indicate that the presence of the E681K mutation increases the extension rate of a G46D F667Y enzyme by 3- to 4.3-fold.

EXAMPLE IV

Cycle Sequencing with G46D F667Y E681K Taq DNA Polymerase and Fluorescein Labeled ddNTPs This example demonstrates the application of the modified polymerase of the invention to fluorescein dye labeled dideoxy terminator cycle sequencing, utilizing 1 µM or less ddNTP and a ratio of ddNTP:dNTP of at least 1:100. The fluorescein dye labeled dideoxy terminators are reagents from the Applied Biosystems PRISM Sequenase® Terminator Sequencing Kits (Perkin-Elmer, Norwalk, Conn.) and were optimized for use with Sequenase DNA polymerase and alpha-thio dNTPs. Cycle sequencing reactions were performed in a 20 µl volume containing 50 mM Tris-HCl (pH 8.8), 2.0 mM MgCl$_2$, 100 µM each dATP, dCTP, and dTTP (Perkin-Elmer, Norwalk, Conn.), 500 µM dITP (Pharmacia Biotech, Piscataway, N.J.), 0.2 µM13 mp18 single-strand DNA template (Perkin-Elmer), 0.15 µM LacZ Forward Primer (Perkin-Elmer), 5 units of G46D F667Y E681K Taq DNA polymerase, 20 units of rTth Thermostable Pyrophosphatase (U.S. Ser. No. 08/528,384), 0.05 µM Sequenase A Dye Terminator, 0.80 µM Sequenase C Dye Terminator, 0.08 µM Sequenase G Dye Terminator, and 1.0 µM Sequenase T Dye Terminator. All four Sequenase Dye Terminators were purchased from Perkin-Elmer. Reactions were placed in a preheated (75° C.) Perkin-Elmer GeneAmp® PCR System 9600 thermal cycler and subjected to 25 cycles of 96° C. for 10 seconds, 50° C. for 5 seconds, and 60° C. for 4 minutes. Dye labeled fragments were purified with Centri-Sep™ columns (Princeton Separations, Adelphia, N.J.) following the manufacturer's instructions and dried in a vacuum centrifuge. Pellets were resuspended in 6 µl of deionized formamide:50 mg/mL Blue dextran (in 25 mM EDTA, pH 8.0) 5:1 (v/v), heated at 90° C. for 3 minutes, and directly loaded onto a pre-electrophoresed 4% polyacrylamide/6 M urea gel and electrophoresed and analyzed on a Perkin-Elmer ABI PRISM' 377 DNA Sequencer according to the manufacturer instructions (ABI PRISM 377 DNA Sequencer User's Manual). Automated base-calling by the Perkin-Elmer ABI PRISM 377 DNA Sequencer analysis software resulted in greater than 98.5% accuracy for 450 bases (6 errors for bases +10 to +460 from primer).

We claim:

1. A method of DNA sequencing which comprises:
   a) providing a thermostable DNA polymerase characterized in that
      i) said thermostable DNA polymerase comprises:
         the amino acid sequence LeuSerXaaXaaLeuXaaXaaProXaaXaaGlu (SEQ ID NO: 1), whereby "Xaa" at positions 3, 9, and 10 of said sequence are any amino acid residue, "Xaa" at position 4 is Lys, "Xaa" at position 6 is Ala or Ser and "Xaa" at position 7 of said sequence is Ile, and
      ii) said thermostable DNA polymerase has a level of discrimination against incorporation of nucleotides labeled with a cyanine dye which is reduced in comparison to a polymerase whose sequence is identical to that of said thermostable DNA polymerase except that "Xaa" at position 4 is Glu;
   b) providing a dye-terminator labeled with a cyanine dye; and
   c) performing a dye-terminator sequencing reaction.

2. A method of producing labeled DNA which comprises:
   a) providing a thermostable DNA polymerase characterized in that
      i) said thermostable DNA polymerase comprises:
         the amino acid sequence LeuSerXaaXaaLeuXaaXaaProXaaXaaGlu (SEQ ID NO: 1), whereby "Xaa" at positions 3, 9, and 10 of said sequence are any amino acid residue, "Xaa" at position 6 is Ala or Ser and "Xaa" at position 7 of said sequence is Ile and "Xaa" at position 4 is Lys, and
      ii) said thermostable DNA polymerase has a level of discrimination against incorporation of nucleotides labeled with a cyanine dye which is reduced in comparison to a polymerase whose sequence is identical to that of said thermostable DNA polymerase except that "Xaa" at position 4 is Glu;
   b) providing a nucleotide labeled with a cyanine dye; and
   c) performing a DNA synthesis reaction.

3. A method of producing labeled primer extension products which comprises:
   a) providing a thermostable DNA polymerase characterized in that
      i) said thermostable DNA polymerase comprises:
         the amino acid sequence LeuSerXaaXaaLeuXaaXaaProXaaXaaGlu (SEQ ID NO: 1), whereby "Xaa" at positions 3, 9, and 10 of said sequence are any amino acid residue, "Xaa" at position 6 is Ala or Ser and "Xaa" at position 7 of said sequence is Iie and "Xaa" at position 4 is Lys,
      ii) said thermostable DNA polymerase has a level of discrimination against incorporation of nucleotides labeled with a cyanine dye which is reduced in comparison to a polymerase whose sequence is identical to that of said thermostable DNA polymerase except that "Xaa" at position 4 is Glu;
      iii) said polymerase also comprises the second amino acid sequence SerGlnIleXaaLeuArg(Val/Ile) (SEQ ID NO: 18) where "Xaa" is any amino acid except Glu, and
      iv) said polymerase has a level of discrimination against incorporation of ribonucleotides labeled with a cyanine dye which is reduced in comparison to the polymerase whose sequence is identical to that of said thermostable DNA polymerase except that "Xaa" at position 4 is Glu; and
   b) providing a ribonucleotide labeled with a cyanine dye; and
   c) performing a primer extension reaction.

4. The method of claim 1, wherein said amino acid sequence comprises LeuSerGlnXaaLeuAlaIleProTyrGluGlU (SEQ ID NO:3), whereby "Xaa" at position 4 is Lys.

5. The method of claim 2, wherein said amino acid sequence comprises LeuSerGlnXaaLeuAlaIleProTyrGluGlU (SEQ ID NO:3), whereby "Xaa" at position 4 is Lys.

6. The method of claim 3, wherein said amino acid sequence comprises LeuSerGlnXaaLeuAlaIleProTyrGluGlu (SEQ ID NO:3), whereby "Xaa" at position 4 is Lys.

7. The method of claim 6, wherein the "Xaa" at position 4 of the thermostable DNA polymerase is Lys.

8. The method of claim 1, wherein said native form is a polymerase from a bacterium selected from the group consisting of: *Thermus thermophilus*, *Thermus* specie Z05, *Thermus* Specie sps 17, *Thermus caldophilus*, and *Thermus filiformis*.

9. The method of claim 2, wherein said native form is a polymerase from a bacterium selected from the group consisting of: *Thermus thermophilus*, *Thermus* specie Z05, *Thermus* Specie sps 17, *Thermus caldophilus*, and *Thermus filiformis*.

10. The method of claim 3, wherein said native form is a polymerase from a bacterium selected from the group consisting of: *Thermus thermophilus*, *Thermus* specie Z05, *Thermus* Specie sps 17, *Thermus caldophilus*, and *Thermus filiformis*.

* * * * *